United States Patent
Caballero Murillo et al.

(10) Patent No.: US 10,301,602 B2
(45) Date of Patent: May 28, 2019

(54) PRODUCTION OF VIRUS OCCLUSION BODIES THAT OCCLUDE VIRIONS COMPRISING GENOMES OF DIFFERENT SPECIES OF BACULOVIRUSES THAT CAN BE USED TO COMBAT INSECT PESTS

(71) Applicants: UNIVERSIDAD PÚBLICA DE NAVARRA, Pamplona, Navarra (ES); CONSEJO SUPERIOR DE INVESTIGACIONES CIENTÍFICAS, Madrid (ES); INSTITUTO DE ECOLOGÍA, A.C., Xalapa, Veracruz (MX); ASSOCIATION POUR LA RECHERCHE ET LE DEVELOPPEMENT DES METHODES ET PROCESSUS INDUSTRIES (ARMINES), Paris (FR)

(72) Inventors: Primitivo Caballero Murillo, Navarra (ES); Inés Beperet Arive, Navarra (ES); Oihane Simón De Goñi, Navarra (ES); Trevor Williams, Veracruz (MX); Miguel Lopez-Ferber, Paris (FR)

(73) Assignees: UNIVERSIDAD PÚBLICA DE NAVARRA, Navarra (ES); CONSEJO SUPERIOR DE INVESTIGACIONES CIENTÍFICAS, Madrid (ES); INSTITUTO DE ECOLOGÍA, A.C., Veracruz (MX); ASSOCIATION POUR LA RECHERCHE ET LE DEVELOPPEMENT DES METHODES ET PROCESSUS INDUSTRIELS (ARMINES), Paris (FR)

( * ) Notice: Subject to any disclaimer, the term of this patent is extended or adjusted under 35 U.S.C. 154(b) by 0 days.

(21) Appl. No.: 15/024,207

(22) PCT Filed: Sep. 23, 2013

(86) PCT No.: PCT/EP2013/069678
§ 371 (c)(1),
(2) Date: Mar. 23, 2016

(87) PCT Pub. No.: WO2015/039704
PCT Pub. Date: Mar. 26, 2015

(65) Prior Publication Data
US 2016/0230148 A1    Aug. 11, 2016

(51) Int. Cl.
*C12N 7/00*       (2006.01)
*A01N 63/00*    (2006.01)

(52) U.S. Cl.
CPC ............... *C12N 7/00* (2013.01); *A01N 63/00* (2013.01); *C12N 2710/14051* (2013.01);
(Continued)

(58) Field of Classification Search
None
See application file for complete search history.

(56) References Cited

U.S. PATENT DOCUMENTS 5,071,748 A * 12/1991 Miller .................. A61M 5/486
435/183

FOREIGN PATENT DOCUMENTS

JP         3-24006 A      2/1991

OTHER PUBLICATIONS

Lasa et al., "Insecticidal Properties and Microbial Contaminants in a Spodoptera exigua Multiple Nucleopolyhedrovirus (Baculoviridae) Formulation Stores at Different Temperatures," J. Econ. Entomol. 101(1): 42-49 (2008).*

(Continued)

*Primary Examiner* — M Franco G Salvoza
(74) *Attorney, Agent, or Firm* — Birch, Stewart, Kolasch & Birch, LLP

(57) ABSTRACT

Production of virus occlusion bodies that occlude virions comprising genomes of different species of baculoviruses (Continued)

that can be used to combat insect pests. A method is presented for the production of occlusion derived virions (ODVs) that simultaneously comprise genomes of different baculovirus species, occluded in a viral occlusion body (OB) with the structural and morphological features characteristic of baculoviruses. Mixed genome ODVs and OBs can be produced by co-infecting insect cells or insect hosts using two or more different baculoviruses species. Co-infection may be achieved by simultaneous inoculation of the different baculoviruses or with a time interval between inoculations, which results in different proportions of each species' genomes in the ODVs and OBs that are produced. The produced OBs can be used either directly for preparing an insecticide, or to infect susceptible insects to produce larger quantities of mixed genome ODVs and OBs, also useful for combating pest insects.

37 Claims, 6 Drawing Sheets

Specification includes a Sequence Listing.

(52) U.S. Cl.
CPC .............. *C12N 2710/14121* (2013.01); *C12N 2710/14131* (2013.01); *C12N 2710/14151* (2013.01)

(56) References Cited

OTHER PUBLICATIONS

Salem et al., "AcMNPV enhances infection by ThorNPV in Sf21 cells and SeMNPV in Hi5 cells," Arch Virol 157: 1875-1885 (2012).*
McClintock et al., "Superinfection of baculovirus-infected gypsy moth cells with the nuclear polyhedrosis viruses of Autographa californica and Lymantria dispar," Virus Research 7: 351-364 (1987).*
Simon et al., "Virus entry or the primary infection cycle are not the principal determinants of host specificity of *Spodoptera* spp. Nucleopolyhedroviruses," Journal of General Virology 85: 2845-2855 (2004).*
Harrison, "Structural divergence among genomes of closely related baculoviruses and its implications for baculovirus evolution," Journal of Invertebrate Pathology 101: 181-186 (2009).*
Clavijo et al., "Mixed Genotype Transmission Bodies and Virions Contribute to the Maintenance of Diversity in an Insect Virus," Proc. R. Soc. B, vol. 277, No. 1665, 2010, (Published online Nov. 25, 2009), pp. 943-951 (Total 10 pages), XP-55085879A.
International Search Report and Written Opinion of the International Searching Authority (forms PCT/ISA/210, PCT/ISA/237 and PCT/ISA/220), dated Dec. 2, 2013, for International Application No. PCT/EP2013/069678.
Kemp et al., "Detection of Single and Mixed Covert Baculovirus Infections in Eastern Spruce, Budworm, Choristoneura Fumiferana Populations," Journal of Invertebrate Pathology, vol. 107, No. 3, 2011 (Available online May 15, 2011), pp. 202-205, XP-28255325A.

\* cited by examiner

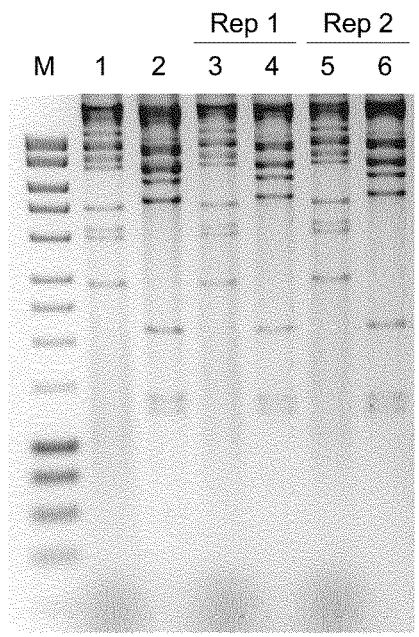
Fig. 2
Fig. 3
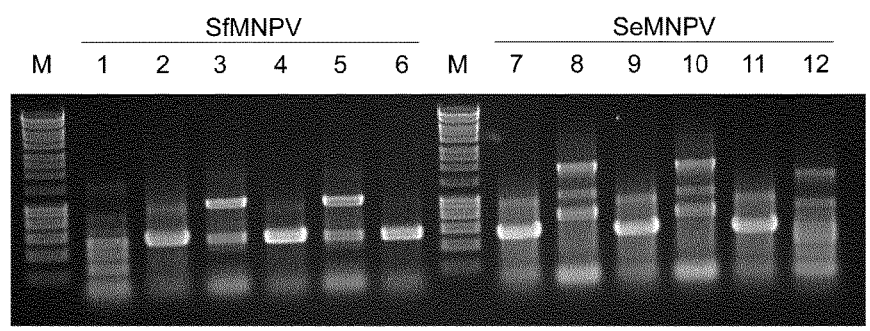
Fig. 4

Fig. 5

PRODUCTION OF VIRUS OCCLUSION BODIES THAT OCCLUDE VIRIONS COMPRISING GENOMES OF DIFFERENT SPECIES OF BACULOVIRUSES THAT CAN BE USED TO COMBAT INSECT PESTS

FIELD OF THE INVENTION

The invention pertains to the field of the production and use of biological insecticides to control infestations of pest insects that are susceptible to particular species or strains of baculoviruses. More particularly, the invention relates to a method for producing mixed virus occlusion derived virions (ODV) that comprise genomes from at least two different baculovirus species co-wrapped in the same virion, and/or for producing virus occlusion bodies (OBs) wherein at least one of said mixed virus occlusion derived virions is occluded, as well as to such ODVs and OBs, the composition comprising them and their use to combat insect pests.

BACKGROUND OF THE INVENTION

Baculoviruses (family Baculoviridae) are insect pathogens that represent an important mortality factor in natural populations of diverse species of insects, including pests of agriculture and medical or veterinary importance. Baculoviruses are classified into one of four genera: Alphabaculovirus (nucleopolyhedroviruses [NPV] of Lepidoptera), Betabaculovirus (granuloviruses [GV] of Lepidoptera), Gammabaculovirus (NPVs of Diptera) and Deltabaculovirus (NPVs of Hymenoptera). Certain baculoviruses have insecticidal characteristics, such as their pathogenicity (as measured by lethal dose metrics), virulence (speed of kill), and occlusion body (OB) production that has led to their development as the basis for biological insecticides on an industrial scale. These products are being used successfully in the control of insect pests (Moscardi 1999). Particularly successful examples of pest control using an alphabaculovirus as a biological insecticide include the control of *Anticarsia gemmatalis* in soya (Moscardi 1999) or *Helicoverpa armigera* in cotton (Sun & Peng, 2007).

Another useful feature of baculoviruses is their high level of biosecurity and the very high expression of particular genes in cell culture in vitro systems which had led to their development as transgene expression vectors (Summers and Smith, 1987; van Oers, 2011). Most baculovirus expression systems are based on the use of *Autographa californica* MNPV (Rohrmann, 2008). Recombinant baculoviruses (rBac) are currently used for the production of hundreds of eucaryotic proteins in insect cells due to their advantages in post-translational protein modification systems that they share with higher animals, including man (Miller et al., 1997; Ahn et al., 2008). rBac-produced proteins are used in functional studies (van Oers, 2011), to improve the insecticidal properties of these viruses (Jiang et al., 2008), in the production of human vaccines (Harper et al., 2009; Kantoff et al., 2010; Madhan et al., 2010), in the development of diagnostic tools and most recently as potential gene therapy vectors (Hitchman et al., 2011; Kaikkonen et al., 2011).

Baculoviruses are double-stranded DNA viruses that replicate in the nucleus of insect cells. The circular genome varies between 80 and 180 kbp depending on the species of virus and is supercoiled and condensed in a protein nucleocapsid (Rohrmann, 2008). The nucleocapsid (NC) acquires an external membrane during assembly and maturation, which results in the formation of the virion, which is the principal infectious entity of baculoviruses (FIG. 1). The biological cycle of baculoviruses involves two morphologically and functionally distinct virions: (1) budded virions (BV) bud from the membranes of infected cells into the insect haemocoel and disperse to infect other cells in tissues and organs that are susceptible to infection in the infected insect, (2) occlusion derived virions (ODV) are occluded in a proteinaceous matrix that forms the occlusion body (OB) that protects ODVs in the environment and facilitate insect-to-insect transmission. The OBs of alphabaculoviruses comprise polyhedrin protein and generally occlude dozens of ODVs. These viruses fall into one of two types (FIG. 1): (i) single nucleocapsid nucleopolyhedroviruses (SNPV) comprise a single nucleocapsid within each ODV, or (ii) multiple nucleocapsid nucleopolyhedroviruses (MNPV) may comprise one or various nucleocapsids within each ODV.

Baculoviruses are capable of productive infection only in arthropod hosts, the majority of which are Lepidoptera. Pathogenic effects have not been observed following the ingestion or injection of baculoviruses in vertebrates, moluscs or plants. As such, baculoviruses are considered extremely safe for the development of biological control agents, as their use involves minimal risks to human health or that of other animals, with the exception of the target pest insect (Burges et al., 1980; Leuschner et al., 2010).

One important issue in the commercialization of baculovirus-based insecticides is the high host specificity of these viruses, that often can only infect and kill a single or a few very closely related species of pests (Griner, 1986). As a result, in crop protection situations in which a complex of two or more pest species has to be controlled, it is invariably necessary to apply OBs of two or more different baculoviruses simultaneously or in separate applications. The production of biological control agents for control of multiple species of pests almost invariably involves the production of multiple species of baculoviruses in different insect colonies, each of which involves its own costs, so that biological control using multiple virus species is not competitive with the cost of control compared to the use of a broad spectrum synthetic insecticide.

Baculovirus OBs can be also be obtained from cultures of susceptible insect cells, both in monolayer cultures and in suspension cultures. Baculoviruses can be used as foreign gene expression vectors, thus obtaining large amounts of recombinant protein, with relative ease, particularly from insect cell cultures, but also from insects larvae (see presentation "Baculovirus expression system" of Yadav et al. available at world wide web.pittedu/-super7/32011-33001/32731.ppt or at the review of Jarvis D L (2009)).

It is now possible to modify the insecticidal characteristics of baculoviruses by the insertion, deletion or interchange of genes from other viruses, from the host insect genome, or from genomes of other organisms or synthetic genes (Inceoglu et al., 2006). The development of baculoviruses with an extended host range has been the subject of study, and in some cases, genetic modification has been employed to influence the ability of the virus to initiate a productive infection in host species that are not naturally permissive to a particular baculovirus. As a first step, the host range of *Autographa californica* MNPV was extended through recombination in the region of the helicase gene to include the silkmoth *Bombyx mori* (Kondo and Maeda, 1991; Croizier et al., 1992, Kamita and Maeda, 1996; Argaud et al., 1998). Subsequent studies employed similar approaches to study the genetic factors that determine host range in baculoviruses (Watanabe et al., 2010). Overall, these studies have concluded that the genes involved in host range are not readily identified and specific genetic modifications necessary to extend host range to include a specific pest insect remain unclear.

An individual insect cell can be simultaneously infected by more than one virus (Garzon and Kurstak 1972; Arella et al., 1983; Kanthong et al., 2010). In baculoviruses, co-infection of insects by two genotypes of the same species of virus, one wild-type and one genetically modified, can favour the persistence of the modified genotype in the environment (Hamblin et al. 1990). In this latter case, two genotypes of the same virus species were involved. The authors of the study suggest that co-occlusion occurred, although in reality only co-infection was demonstrated.

A similar approach was described in the family of WO 88/02030 and U.S. Pat. No. 5,071,748 (Miller, 1991). The invention described in said documents relates to a polyhedral inclusion body (PIB, which is a synonym of occlusion body, OB) containing a mixture of nucleocapsids of at least two genetically distinct baculoviruses. The mixed composition of PIBs (mPIB) contains nucleocapsids of at least one "recombinant" baculovirus which is incapable of directing the production of polyhedrin in infected insect cells and nucleocapsids of at least one baculovirus which may be a wild-type, mutant or genetically modified virus, which is capable of directing the production of polyhedrin in infected cells. Although, in principle, the invention was compatible with the use of genotypes of different species of baculoviruses, the only example provided describes the infection of insect cells with two genotypes of the same species, the nuclear polyhedrosis virus that infects *Autographa californica*, AcMNPV (abbreviated in the mentioned documents as AcNPV). One of the used viruses is a wild-type virus and the other one is a recombinant virus, the L-1 variant of AcMNPV, in which the polyhedrin gene is replaced by a cDNA encoding human tissue-type plasminogen activator. According to Example 2 of WO 88/02030, the infection of *Heliothis virescens* caterpillars with the obtained mPIB gives rise to progeny PIBs containing nucleocapsids of both AcMNPV genotypes. In this particular case, the ratio of the wild type virus increased relative to the original ratio, a gradual increase ratio of wild type virus being found after serial passage through caterpillars of subsequent mPIB progeny. The described assays do not mention explicitly whether the obtained PIBs contained virions wherein nucleocapsids of both genotypes were co-occluded or not; this key issue was not verified.

Thus, in essence, the information presented by Hamblin et al. (1990) or Miller (WO 88/02030) indicates that both genotypes used were present and persisted in the experimental inoculum, but they failed to present evidence of a physical association between the genotypes; specifically, that both genotypes were present in a single OB (PIB) or that both genotypes were present in a single ODV.

Other authors (López-Ferber et al., 2003), have found co-occlusion in a single virion of different genotypes of the same species but, as in the previous cases, at least one of the genotypes was a defective one that lacked genes essential for survival. Therefore, the defective genotype depends on the co-infection with complete virus genotypes and of the use of gene products of the latter for their replication and transmission. More recently, it has been demonstrated that different genotypes of a virus species can be present in an ODV that is subsequently occluded in an OB (Clavijo et al., 2009), i.e., nucleocapsids, each containing a distinct genotype, can be wrapped together in a membrane to form a mixed genotype ODV.

Co-infection of a single insect by two species of baculoviruses has been described in experiments involving *Autographa californica* MNPV (AcMNPV) and *Spodoptera exigua* MNPV (SeMNPV) (Yanase et al. 1998). This study concluded that one of these viruses did not replicate and generation of recombinants within the infected insect was not observed. Similarly, in cell culture studies, co-infections by two different species of baculoviruses have been reported, principally in terms of the pathological implications for the cells and each of the viruses involved (McClintock & Dougherty 1987; Salem et al., 2012)

Subsequent work by Simón et al. (2004) has shown that, under certain conditions, two different species of nucleopolyhedroviruses (*S. exigua* MNPV and *S. frugiperda* MNPV) can interact to facilitate the co-infection of larvae of *S. frugiperda* that are not susceptible to *S. exigua* MNPV when inoculated alone. However, that study did not present evidence that both these viruses could replicate simultaneously in the same cell or that co-infection by these viruses could result in mixed virus ODVs or co-occluded mixed virus OBs.

Therefore, the prior art, such as the work reported by Yanase and coworkers (Yanase et al., 1998), indicates that baculoviruses belonging to different species might co-infect a same insect, but no evidence has been presented for the production of mixed ODVs containing nucleocapsids of both species, which are occluded into the same OB. However, it would be useful to prepare insecticide compositions based on baculoviruses containing more than one different species, that could be used for crops that are susceptible to infestation by more than one species of insects or by insects that show variable susceptibility to different genotypes of the same baculovirus, in order to avoid separate applications of insecticide and to combat insect pests, particularly when more than one insect species is present. Moreover, such compositions should be produced using a method that allows the compositions to be competitive with the costs associated to the use of a broad spectrum synthetic insecticide. Preferably, the production method should avoid the production of multiple species of baculoviruses in different insect colonies, each of which involves its own costs.

The present invention provides a solution to such problem.

SUMMARY OF THE INVENTION

The present invention is based on the evidence disclosed in the present application, that two phylogenetically closely related baculoviruses (for instance, SeMNPV and SfMNPV), as well as two distantly related baculoviruses (like, for instance, AcMNPV and SfMNPV), can co-infect and each produce a productive infection in a particular insect cell. This results in mixed virus ODVs that are occluded into OBs. The mixed virus OBs have an extended host range phenotype and can be used to combat the target pests using a single OB inoculum.

Thus, in a first aspect, the present invention refers to a method for producing mixed virus occlusion derived virions (ODV) that comprise genomes from at least two different baculovirus species co-wrapped in the same virion, and/or for producing virus occlusion bodies in which at least one of said mixed virus occlusion derived virions is occluded. Preferably, at least two of the different genomes present in the same ODV are genomes that are each capable of giving rise to an infective baculovirus particle, capable of producing a complete viral cycle in a cell, without the need for co-infection with a second baculovirus comprising a different genome. It is preferred that virus occlusion bodies are produced. It is particularly preferred that the virus occlusion bodies are produced by:
  a. co-infecting larvae or culture cells of an insect species with the baculovirus genomes to be co-wrapped in at least one of the produced occlusion derived virions, wherein each baculovirus genome belonging to one particular species can be in the same or in a different ODV than the other one;
  b. rearing the infected larvae or cultivating the cells until death by polyhedrosis;
  c. isolating the produced OBs from the larvae or cultivated cells after their death;
wherein the cells or larvae are susceptible to infection by either of the baculoviruses whose genomes are to be co-wrapped in at least one of the produced occlusion derived virions.

Another aspect of the present invention is a mixed virus occlusion derived virion (ODV) that comprises genomes of at least two different baculovirus species co-wrapped in the same virion: an ODV of the present invention. A particular preferred embodiment of that aspect of the invention are the ODVs obtained by the method of the present invention.

Similarly, it is also an aspect of the present invention a mixed virus occlusion body (OB) which has occluded at least an ODV comprising genomes of at least two different baculovirus species co-wrapped in the same virion: a mixed OB of the present invention. A particular preferred embodiment of that aspect of the invention is a mixed OB obtained by the method of the present invention.

Another aspect of the present invention is a composition comprising at least an ODV of the present invention and/or at least an OB of the present invention. Such a composition is a composition of the present invention.

Also an aspect of the present invention is the use of the OBs of the present invention and/or a composition of the present invention for the combat of insect pests.

BRIEF DESCRIPTION OF THE FIGURES

FIG. 2. Restriction endonuclease profiles generated following treatment of *Spodoptera exigua* nucleopolyhedrovirus variant SeUS2-A (lane 1) and *Spodoptera frugiperda* nucleopolyhedrovirus variant SfNIC-C(2) genomic DNA with PstI. Molecular marker (M) is Hyperladder I (Bioline)

FIG. 3. Restriction fragment length polymorphism of virus genomic DNA following treatment with PstI of DNA extracted from OBs and electrophoresis. Lanes:
  M: molecular weight marker Hyperladder I (Bioline)
  Lane 1: PstI restriction profile of DNA extracted from SeUS2-A OBs.
  Lane 2: PstI restriction profile of DNA extracted from SfNIC-C OBs.
  Lane 3: PstI restriction profile of DNA extracted from OBs produced following co-infection of *S. exigua* larvae with SeUS2-A and SfNIC-C ODVs. Only the profile of SeUS2-A is observed, although PCR amplification confirmed the presence of SfNIC-C DNA (data shown is from repetition #1).
  Lane 4: PstI restriction profile of DNA extracted from OBs produced following inoculation of *S. frugiperda* second instars using OBs produced during co-infection by SeUS2-A and SfNIC-C ODVs.
  Lane 5: Same as lane 3, but data shown for repetition #2.
  Lane 6: Same as lane 4, but data shown for repetition #2.

FIG. 4: PCR detection of SeUS2-A and SfNIC-C DNAs extracted from OBs produced in *Spodoptera exigua* or *S. frugiperda* larvae using specific primers targeted at ie-O gene sequences.

M: molecular weight marker Hyperladder I (Bioline)

Lane 1: DNA extracted from SeUS2-A OBs (no specific amplification product)

Lane 2: DNA extracted from SfNIC-C OBs

Lane 3: DNA extracted from OBs produced following co-infection of *S. exigua* larvae with SeUS2-A and SfNIC-C ODVs. Results from repetition #1.

Lane 4: DNA extracted from OBs produced following inoculation of *S. frugiperda* second instars using OBs from larvae co-infected with SeUS2-A and SfNIC-C ODVs. Results from repetition #1.

Lane 5: Same as lane 3, but results from repetition #2.

Lane 6: Same as lane 4, but results from repetition #2.

FIG. 5. Co-occlusion of SeUS2-A and SfNIC-C viruses in OBs: relative abundance of SfNIC-C genome per 100 ng of SeUS2-A genome in different OB mixtures. The corresponding number of passage (P0 to P6) in *Spodoptera exigua* larvae is indicated below the x-axis, P0 corresponding to co-infection using ODVs released from 1:1 ratio mixtures of SeUS2-A and SfNIC-C OBs. Error bars indicate the standard deviation.

FIG. 6: Electrophoresis of PCR products amplified from AcC6 (AcMNPV), SfNIC-B (SfMNPV) and DNA extracted from co-occluded mixed virus OBs (AcMNPV+SfMNPV). Hyperladder I indicates a molecular size marker with fragment length indicated on the left.

FIG. 7. Diagrammatic example of mixed virus ODVs occluded in mixed virus OBs produced following co-infection of *S. frugiperda* larvae with SfNIC-C and AcC6 viruses. The rectangles and circles represent ODVs in frontal (side) or top (end) view, respectively. The horizontal lines inside the rectangles or the dots inside the circles represent nucleocapsids, the dark ones belonging to one species and the lighter ones belonging to another species.

FIG. 8: Electrophoresis of PCR products amplified from DNA extracted from end point dilution samples (3 repetitions). Hyperladder I indicates molecular size marker (Bioline). The final two lanes indicate positive controls for AcC6 (AcMNPV) and SfNIC-B (SfMNPV) genomic DNA. Upper lanes indicate amplifications using SfNIC-B specific primers, whereas lower lanes indicate amplifications using AcC6 specific primers.

FIG. 9: Larval mortality observed following single, simultaneous or delayed superinfection of *S. frugiperda* larvae. Treatments are indicated by the initials of the first virus, the interval in hours between first and second inoculation and the initials of the second virus inoculated, e.g., Ac12Sf indicates larvae initially infected with AcC6 OBs and subsequently inoculated 12 hours later with SfNIC-B OBs. Values above columns indicate percentage of virus induced mortality. Values followed by identical letters did not differ significantly (ANOVA, Tukey, p>0.05).

DETAILED DESCRIPTION OF THE INVENTION

Figure 1:
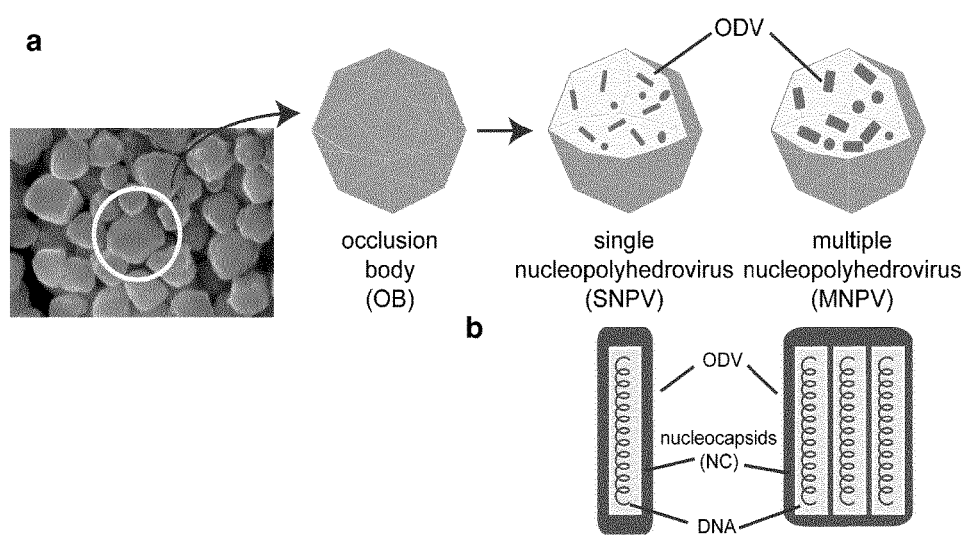
FIG. 1 shows the microscopic structure of nucleopolyhedroviruses.
  Panel a (upper part of the figure) shows a micrograph of occlusion bodies (OB), whose individual schematic representation is shown on the right to the micrograph. On the right side of the panel, two occlusion bodies are represented, showing their interior, in which the circles and rectangles represent ODVs (occlusion derived virions).
  Panel b (lower part of the figure) represent two different types of ODVs. The one of the left, corresponding to a single nucleopolyhedrovirus (SNPV) contains one single nucleocapsid (NC), formed by the genomic DNA (represented as a helix) and the associated proteins. The one on the right, corresponding to one multiple nucleopolyhedrovirus (MNPV) contains one or more than one nucleocapsid (NC) (each of which is shown as a rectangle with a helix inside) per ODV.

A method is presented by which virions comprising genomes of different baculovirus species, occluded within the same viral occlusion body (OB), with the structural and morphological features that are characteristic of baculoviruses, can be obtained. Mixed genome OBs obtained by the method of the present invention contain a mixture of two or more different genomes from different species or strains of baculoviruses.

Contrary to the results found in previous studies, such as that of Yanase and coworkers (Yanase et al., 1998), the assays presented in the present application show that the coinfection of a single insect by two species of baculoviruses, specifically two species of multiple nucleopolyhedroviruses, can result in the replication of both viruses in the same cells and, even, to the packaging of nucleocapsids containing different viral genomes in the same occlusion derived virion (ODV).

Thus, the different genomes can be present simultaneously in individual ODVs, which can be produced by co-infection of an insect species that is susceptible to infection by two or more species of baculoviruses that differ in their insecticidal characteristics, such as pathogenicity, virulence, production of OBs and host range. They may be occluded in virus occlusion bodies (OB) with normal morphology and size, and can infect species of insects susceptible to infection by either of their component baculoviruses.

ODVs comprising more than one nucleocapsid (and, therefore, more than one baculovirus genome) are characteristic of multiple nucleopolyhedroviruses, whereas single nucleopolyhedroviruses are characterized by the presence of only one nucleocapsid in each ODV. Therefore, in order to carry out the method of the present invention, at least one of the baculoviruses used must be a multiple nucleopolyhedrovirus (MNPV).

The examples of the present application show that the method of the present invention can work both with phylogenetically closely related baculoviruses (for instance, SeMNPV and SfMNPV), and with distantly related baculoviruses (like, for instance, AcMNPV and SfMNPV). In both cases, the baculoviruses can co-infect and each produce a productive infection in a particular insect cell. According to the available knowledge about baculoviruses, the method of the present invention can be carried out with any combination of baculoviruses, provided that at least one of them is a multiple nucleopolyhedrovirus. It is preferred that all baculoviruses inoculated to a same larva are alphabaculoviruses, as in the examples of the present application. The alphabaculoviruses can belong to the same phylogenetic group (as in Example 1, wherein two alphabaculoviruses belonging to Group II are used) or to different groups (such as in Examples 2 and 3, wherein one alphabaculovirus of Group I and one alphabaculovirus of Group II are used).

Examples of possible combinations can be found in said Examples: *Spodoptera frugiperda* is a destructive lepidopteran pest of several economically important crops. As *Spodoptera frugiperda* multiple nucleopolyhedrovirus (SfMNPV) has a very narrow host range (in fact, it can produce a lethal infection in *Spodoptera frugiperda, Spodoptera litura* and *Spodoptera exigua*), it is advisable to use it in combination with insecticidal agents with a broader spectrum to control more pest species with a single control agent. To that aim, *Autographa californica* multiple nucleopolyhedrovirus (AcMNPV), that can infect and kill the larvae of at least 32 lepidopteran species, including *S. frugiperda*, seems to be an interesting partner. However, not all host species are highly susceptible to fatal infection by AcMNPV. Example 3 shows that simultaneous infection of AcMNPV with SfMNPV can increase the mortality obtained in insects treated with AcMNPV; thus, compositions comprising OBs containing mixed ODVs with genomes of each of said two viruses can improve the results obtained.

The method of the present invention can be carried out by co-infecting insect larvae or insect cell cultures with the baculovirus genomes that are to be co-wrapped in at least one occlusion derived virion (ODV).

In the method of the present invention, the baculovirus genomes are provided (inoculated) to the insect larvae or to the insect cell cultures preferably forming nucleocapsids. The inoculated nucleocapsids can be associated in groups wrapped by an envelope forming ODVs, or can form budded virions (BV), which, as explained above, are the virus particles that are produced in vivo for cell-to-cell transmission of the infection within the infected insect or in cell culture. In turn, inoculated ODVs can be free ODVs (not occluded in occlusion bodies) or they can be occluded in a proteinaceous matrix forming occlusion bodies (OB), each OB containing several ODVs.

Insects and cell cultures can be inoculated using BVs. When BVs are inoculated, several different sets of BVs must be inoculated; each set of BVs contains nucleocapsids with the genome of a particular baculovirus species. The number of BV sets to be inoculated will be equal to the number of different baculovirus species genomes that are be co-wrapped in a same ODV. Thus, the use of BVs as inoculum necessarily implies that BVs containing genomes (nucleocapsids) of one of the virus types and BVs containing genomes (nucleocapsids) of the other virus type (or types) to be co-wrapped in a same ODVs should be inoculated.

As each BV contains a single nucleocapsid and each nucleocapsid contains a single genome copy, carrying out the method of the present invention by inoculating nucleocapsids of different species of baculoviruses that are in the form of BVs of different baculovirus species is similar to another possible embodiment wherein nucleocapsids containing individual copies of a particular virus species genome are wrapped to form ODVs and used to inoculate an insect host (an insect larva) or to an insect cell culture. In this embodiment of the method of the present invention, the ODVs with the baculovirus genome belonging to one particular virus species are used to inoculate the insect larvae or the insect cell cultures simultaneously, or following an interval of time, with ODVs or BVs that comprise nucleocapsids containing the genome of another virus species that is different from the first one. Such an embodiment will be preferred, particularly when the method of the invention is carried out for the first time.

But the latter situation is not necessary to carry out the method of the present invention, as can be seen in Example 3, wherein ODVs, occluded in OBs obtained by the application of the steps of the method of the present invention are used to inoculate healthy larvae to obtain new ODVs and OBs and, as can be seen in the Example and the corresponding Figures, some of the ODVs used for the additional rounds of inoculation and OB production contain more than one type of genome, i.e., genomes belonging to the two or more different baculovirus species inoculated in the first round are co-wrapped in some of the ODVs obtained from a first round of infection and can be used to inoculate larvae and carrying out again the method of the present invention.

As previously commented, ODVs (and, therefore, the nucleocapsids wrapped within ODVs) can be used to inoculate insect larvae, being occluded in occlusion bodies (OBs) or not being occluded in occlusion bodies (in the latter case, the ODVs are herein referred as free ODVs). In the case of insect cell cultures, ODVs can be used for inoculation after having been released from OBs. ODVs released from OBs are hereafter referred to as free ODVs.

When OBs are used for the inoculation, all the ODVs occluded in a same occlusion body can belong to a single species, i.e., all ODVs contain nucleocapsids with the genome of a single virus species, and all ODVs contain nucleocapsids with the genome of the same species. But it is also possible that the ODVs included in a same occlusion body have different compositions regarding the genomes inside their nucleocapsids, some of them containing the genomes of a single species, other ones containing the genomes belonging also to the same species, but different from the first one, and still others where different nucleocapsids are wrapped together to form ODVs, wherein at least one, or several ODVs, include(s) a genome belonging to one species different from the species genome of the other nucleocapsids of the same ODV. Both kinds of OBs can be inoculated to carry out the method of the present invention. Therefore, a possible embodiment of the present invention is one wherein the inoculated nucleocapsids are wrapped forming ODVs occluded in occlusion bodies and at least one inoculated occlusion body comprises at least one ODV in which nucleocapsids comprising genomes of more than one baculovirus species are co-wrapped.

Another possible embodiment is that in which all the ODVs occluded in a same occlusion body contain nucleocapsids with the genome of the same species. In the latter case, several sets of OBs should be used to inoculate the insect larvae, each set comprising nucleocapsids containing genomes of a particular virus type or species.

As explained above, BVs or free ODVs can be used for inoculating insect cells for the purposes of the present invention. This depends on the system used for the replication of the inoculated genomes and the production of new virus particles. For inoculation of cultivated insect cells in vitro with different baculovirus species genomes, BVs or free ODVs can be used to infect the cells.

When the insect cells that are to be co-infected with the different baculovirus genomes are part of the tissues of an insect host (an insect larva), BVs, or free ODVs or OBs of different baculovirus species or OBs comprising mixtures of genomes of different baculovirus species can be also used for inoculation, but the inoculation route must be kept in mind to select the kind of particle to use:

When the virus particles containing the baculovirus genomes are injected, BVs or free ODVs can be used. Haemocoelic injection is preferred.

When the nucleocapsids are inoculated to insect larvae orally, BVs, free ODVs or OBs can be used. BVs are the least effective particles for infection by this route. Free ODVs can be used, but it is preferred that these are occluded in occlusion bodies, since occlusion bodies are the virus particles ingested by insect larvae in nature and they are the natural infective particles. When oral inoculation is used, the occlusion bodies can be administered in an aqueous suspension that is provided to the insects, or they can be administered in solid or semi-solid form, mixed with diet or other substances ingested by the insect larva.

Once insect cells of a larva or insect culture cells are infected, they give rise to other nucleocapsids that are subsequently incorporated into ODVs and OBs. In accordance with the present invention, when insects or insect cells are co-infected with genomes of different baculovirus species, a fraction of the produced ODVs are mixed virus ODVs, where at least one of the nucleocapsids contains a genome copy that is different from the other genome copies (the other nucleocapsids) co-wrapped in the same ODV, that is, genomes of different baculovirus species are co-wrapped in the same ODV.

As explained above, the mixed virus ODVs or the OBs in which they are occluded can be used to infect susceptible insects to produce large quantities of mixed genome OBs that can be used as a biological control agent to combat pest insects. This allows an increase in the number of insect species that can be managed using an insecticide containing baculoviruses, so that it is not necessary to apply two different insecticides, each comprising a different baculovirus species, when two or more insect pest species are present (or have to be controlled) on a same plant, crop or cultivation. Importantly, such mixed virus OBs can be obtained from a same insect colony, which avoids multiplying the costs currently associated with the production of multiples species of baculoviruses in different insect colonies, each involving its own costs. This reduces the costs of production of the type of insecticide described in the present invention.

As shown in Example 3 of the present application, in some cases, such as that of the simultaneous infections with two different baculoviruses, the mortality obtained in the infected larvae was higher than that obtained with a particular baculovirus species alone (e.g., compare the mortality obtained with the genotype AcC6 of AcMNPV with the mortality obtained with the simultaneous co-infection with AcC6 in mixtures with the genotype SfNIC-B of SfMNPV). Therefore, the method of the present invention and the compositions with mixed virus OBs of the invention obtained by said method can be useful also in certain cases where only one insect pest species is infesting a plant or crop and there are doubts about the susceptibility of the insect to a particular baculovirus species, because two virus species will increase the probability of killing the insect pest, or also in order to try to increase the prevalence of mortality of the pest and thus the effectiveness of the control measure.

Moreover, co-infection of the host insect may be performed simultaneously or following a particular interval of time between the first inoculation and the inoculation with the second baculovirus species and/or subsequent inoculations. This procedure results in different proportions of each species' genomes in the ODVs and OBs produced in the co-infected insect. In addition, the examples of the present application also show that the order of inoculation of each baculovirus species can affect the proportion of each species' genome in the final OB composition. Thus, simply varying the conditions under which the method of the present invention is performed (time between inoculations and order of inoculation of the different baculoviruses), it is possible to obtain OB compositions with different proportions of each baculovirus.

Another variable that can be changed in the method of the present invention is the proportion of each baculovirus that is used to inoculate the insects. The proportion of the number of inoculated genomes of each baculovirus can be 1:1 or a different one, provided that all baculoviruses that must have a genome copy present in the mixed ODVs or the mixed OBs to be obtained are inoculated.

Therefore, the method of the present invention also allows the production of OB compositions with different proportions of each baculovirus genotype, as desired, by varying the interval of time between the inoculation of the first baculovirus and the inoculation of the second (or a subsequent) baculovirus, and/or the order of inoculation of the different baculovirus (when the viruses are inoculated separately in time) and/or the proportion of genome copies of each baculovirus that are used to inoculate an insect. Thus, both the simultaneous inoculation and the separate inoculation, with an interval of time between the inoculation of a baculovirus and the inoculation of the second (or subsequent) baculovirus are embodiments of the method of the present invention, as well as the inoculation of the same quantity (proportion 1:1) of genome copies for each baculovirus species or the inoculation of a proportion different to 1:1.

The nucleocapsids containing the baculovirus genome belonging to a particular species can be used to inoculate the insect larvae or culture cells separately in time with regard to the nucleocapsids including the other baculovirus genome (or the other baculovirus genomes, when more than two species are inoculated and are expected to have at least one copy of their genomes in the mixed ODVs produced). That embodiment of the method of the present invention is possible when insect larvae or culture cells are inoculated with BVs or with ODVs containing nucleocapsids with the baculovirus genome belonging to a particular species that is different to that of the other inoculated species. When insects are co-infected with two or more baculovirus species by sequential inoculation of the nucleocapsids belonging to each particular species, the delay of time between the first and the last inoculation should be inferior to the time necessary for the manifestation of the signs of the first infection. Usual signs of infection prior to death include lethargy, reduced feeding rate, changes in coloration of the tegument and displacement to the apical parts of host plants in some viruses; the presence of such signs can be considered as an indication of evident disease.

Thus, and in accordance with the results of the assays shown in Example 3, when the different baculoviruses are inoculated separately in time, it is preferable that the time when the second (or final) inoculation takes place is inferior to 48 hours with regard to the inoculation of the nucleocapsids with the genome of a different baculovirus species, and more preferably not more than 24 hours after the inoculation of the first baculovirus, even more preferably not greater than 16 hours. This is because it seems that, as the time after the first inoculation (infection) increases, cells cease to be receptive to a second baculovirus. Therefore, when virions and/or occlusion bodies are to be obtained that contain nucleocapsids of more than one baculovirus species, it is particularly preferred not to delay the inoculation of the second baculovirus more than 16-24 hours after the infection of the first baculovirus.

It is also an embodiment of the method of the present invention that wherein the nucleocapsids with the baculovirus genome belonging to a particular species are used to inoculate cultured insect cells or insect larvae simultaneously with the nucleocapsids that have the other baculovirus genome(s) to be occluded with the first one in at least one occlusion-derived virion. This embodiment is compatible with the nucleocapsids being in the form of BVs, ODVs or OBs and, in this case, both ODVs (free or occluded in OBs) containing only genotypes of the same species and mixed ODVs (ODVs containing genomes of different baculovirus species, wherein at least one of the genomes is different from the other ones). Mixed OBs, as well as OBs in which all occluded ODVs contain genomes belonging to only one species, which is the same species for all co-occluded ODVs, can also be used.

When the method of the present invention is carried out with insect cell cultures, any insect cell line can be used whenever it is susceptible to infection by the both (or more than two) species of baculoviruses whose genomes must be present in the ODVs or OBs that are to be produced. A list of insect cell lines and viruses to which they are susceptible is available in Lynn (2007). Although the cell lines Sf9 and Sf21 from *S. frugiperda* and High5 from *Trichoplusia ni* are the most commonly used, any other insect cell line can be used to obtain mixed ODVs and mixed OBs. Infecting a cell line with ODVs or BVs of a particular species of baculovirus and ODVs or BVs of a different species of baculovirus, both of them infective to that cell line, will conduct to the production of mixed ODVs and mixed OBs. When it is possible to see polyhedra inside most of the infected cells (5-7 days post infection depending on the cell line and the viruses used), both cells and medium has to be harvested. Mixed OBs will then be collected by low speed centrifugation (King et al., 1992).

When an insect host is used to produce OBs, the insect species used in the method of the present invention can be any insect susceptible to the two (or more than two) species of baculoviruses whose genomes must be present in the OBs that are to be produced. The insect should be in the stage of larva, which is the stage in which insects are usually susceptible to baculovirus infection. Insects usually molt several times before reaching the pupal stage; each stage (or sub-stage) between two successive molts are usually known as instar, which denomination is also applied to the individual larvae in a specific instar. The number of instars an insect undergoes depends on the species and the environmental conditions. Larvae in the last possible instars (if possible, at least fourth instars) are usually preferred to produce OBs, because their larger size allows the production of larger quantities of OBs.

As used in the present application, the term "inoculation" refers to the administration of viruses (the "pathogens" of the method of the present invention) to the insects. Such administration can be by direct injection (which is preferred when the viruses are in the form of free virions, not occluded in occlusion bodies) or can occur by ingestion, as happens in nature, wherein larvae ingest baculovirus OBs that are present on the leaves and are ingested with contaminated leaf tissue: this is "oral inoculation" or "inoculation per os". For this second kind of inoculation, either a liquid suspension (preferably aqueous) containing OBs is administered orally to the larvae, for instance, by the droplet feeding method of Hughes and Wood, 1986, as in Examples 2 and 3 of the present application, or the OBs are used to contaminate a substrate that is consumed by the insect larva, such that they are administered, for instance, in solid or semi-solid form, mixed with the diet provided to the larvae.

Then, the method of the present invention can be also defined as a method for producing mixed OBs that comprises the steps of:

a) co-infecting insect larvae with two different baculovirus species, by simultaneous inoculation, or sequential inoculation with a delay of time inferior to the time necessary for the manifestation of the signs of the first infection, and b) rearing the inoculated larvae in the conditions necessary until evident disease or death by polyhedrosis.

The OBs produced by the dead larvae can be isolated purified from the dead larvae by any technique known in the art, such as that including grinding the dead larvae in water, filtering the resulting suspension, allowing or causing (precipitating) the OBs to separate from the suspension and settle down by sedimentation, centrifugation or a related technique (preferably, accelerating the separation of the OBs and the remaining liquid by centrifugation) and separating the pellet of OBs from the supernatant. The isolated OBs can be resuspended in an aqueous solution, giving rise to an aqueous suspension of OBs that can be stored at room temperature or under refrigeration (0° to 6° C.) or under freezing conditions (−80° C. to 00) prior to formulation. Freezing conditions are preferred when the OBs are intended to be stored for a long term. Alternatively, the aqueous suspension of OBs can be lyophilized and stored at room temperature or in refrigeration.

If free (non occluded) ODVs are to be obtained, they can be released from the produced OBs by submitting them to alkaline lysis, for instance using an alkaline solution, as in Example 2.

As previously mentioned, this invention provides, for the first time, a method of producing baculovirus occlusion bodies (OB) which occlude virions that comprise genomes of different baculovirus species. Such OBs can be of use for the biological control of insect pests, as an alternative solution compared to the OBs comprising genomes of only one virus species that are currently commercialized as biological insecticides. Therefore, such OBs wherein at least some of the ODVs comprise genomes of different baculovirus species are also an aspect of the present invention. Also the compositions comprising such OBs are another aspect of the present invention. The use of such OBs, and also of the compositions comprising them, for the biological control of insect pests are another aspect of the present invention, particularly wherein OBs of the present invention are the active ingredient of the formulation intended to be used to combat insect pests.

Upon carrying out the method of the present invention, as can be seen in Example 2, not all ODVs occluded in a mixed OB have necessarily a mixture of genotypes: some of them will contain only nucleocapsids with the genome of one species, other ODVs will contain nucleocapsids in which all the genomes belong to a second species of baculovirus, and a third type will be mixed virus ODVs, wherein genomes of at least two different species will be present in the same virion. An OB with such a mixture of ODVs has been represented in FIG. 7, as an example of an OB of the present invention. It must be noted that all OBs comprising at least one ODV wherein genomes of two or more different species are occluded are encompassed by the scope of the present invention, although it is not necessary that all ODVs present within a same OB contain different genomes for the OB to be an OB of the present invention. Also the OBs wherein each occluded ODV contains genomes of only a single species but wherein ODVs containing the genomes of at least two different species are co-occluded are OBs of the present invention.

Similarly, the compositions of the present invention are those that comprise at least one OB wherein it is occluded at least one ODV comprising genomes of two or more different species that are co-wrapped, and also the compositions that comprise at least one OB wherein ODVs containing nucleocapsids with the genomes of a single species are co-occluded but wherein each ODV belong to a different species. It is not necessary that all OBs have co-occluded baculoviruses of different species for the composition to be encompassed by the scope of the present invention. Indeed, as can be seen in Examples 2 and 3, carrying out the method of the present invention results in progeny OBs wherein at least a fraction of them can contain a single type of virus species genome, that is, some of the OBs can contain genomes of only one of the baculovirus species inoculated and some OBs can contain ODVs wherein each ODV contains genomes of only one genotype but the genotypes of different ODVs included in a same OB can be different. Additionally, the compositions comprising mixed ODVs of the present invention are also compositions of the present invention and are encompassed within the scope of the present invention.

As the occlusion bodies obtained by the method of the present invention have the features that are characteristic of OBs of baculoviruses, they can be extracted and/or purified from the infected larvae in which they have been produced by any technique known in the art, such as the technique of filtration and differential centrifugation used in the examples of the present application. They can be formulated as solid or liquid formulations (for instance, as an aqueous, powder or granular formulation), giving rise to different compositions, as desired, that are suitable for being used to combat infestations of insect pests.

The compositions of the present invention have the characteristic of the number of insect species that they can infect and kill using a single type of OB inoculum compared to either of the component viruses alone. This is achieved using ODVs and OBs that comprise mixtures of different virus species have a host range that differs from that of either of their component virus species alone. Thus, the OBs of the present invention and/or the compositions of the present invention can be used to combat insect pests. Particularly, they can be used to combat two or more insect pest species using a single application of mixed virus OBs or mixed virus ODVs. The substrate that requires protection from or control of pest infestations might be a plant, a crop, a cultivation field, or a stored product or the like, or another substrate that is a source of food for an insect pest. Usually, if OBs or the present invention and/or a composition of the present invention is used to combat an insect pest, they will be the active ingredient (or one of the active ingredients) of the insecticide formulation.

For instance, when the OB compositions are in the form of aqueous suspensions, they can be sprayed onto plants. The OB compositions to be used as biological insecticides can be also applied by other methods, such as aerial spraying, ground spraying, dust application, application in irrigation water, by fogging, misting, or by inoculation of virus-killed insects or parts thereof.

In the OB compositions of the present invention, other compounds can be present, such as agriculturally suitable excipients and/or adjuvants, particularly those compounds that can be considered adjuvants because they facilitate the preparation of the composition to be applied in the appropriate form according to the application method desired. Also the composition may include, for instance, a fertilizer or another pesticide or a compound which is known to potentiate the infectiousness of OBs.

As explained above, free ODVs can also give rise to an infection when they are inoculated orally. Therefore, compositions comprising mixed virus ODVs of the present invention can be also used as biological insecticides, as well as the compositions comprising mixed virus OBs and mixed virus ODVs. The details given above about the use of OB compositions of the present invention to combat insect pests are also applicable to other compositions of the present invention, such as the compositions comprising free mixed virus ODVs and the compositions comprising mixed virus OBs and free mixed virus ODVs: methods of application, substrates to protect from or where to combat pest infestations, other compounds that can be present in the same composition.

As can be seen in Examples of the present application, virions containing genomes of different species can be useful to carry out the method of the present invention, as they can be used to inoculate to the insects (preferably by injection) to produce OBs of the present invention. They can also be of use for co-infection assays or they can be the result of assays that can provide useful information to decide the proportion of each virus species to achieve a mixed OB composition depending on the desired conditions of application and the order of administration of each baculovirus or the delay between the administration of two baculoviruses that is appropriate to obtain mixed OBs with the desired proportion of each baculovirus in the obtained composition of OBs. Thus, occlusion-derived virions (ODVs) comprising the genomes of two or more baculovirus species are also an aspect of the present invention.

The invention will now be explained with more detail with the following Examples and Figures.

EXAMPLES

PCR

PCR assays were performed by using the primers shown in Table 1 below.

TABLE 1

| Primers | Sequences | Localization of fragment to amplfiy (nucleotides in the genome) | Amplification purpose |
| --- | --- | --- | --- |
| Seie0.1 (Forward) | 5'-CTATAGCTCGAC GCTCGGTG-3' (SEQ ID NO: 1) | ie0 gene of SeUS2-A (nt 131937-131959) | Quantification of DNA of SeUS2-A |
| Seie0.2 (Reverse) | 5'-ATCGTCTTCGAT ACCGCGAG-3' (SEQ ID NO: 2) | ie0 gene of SeUS2-A (nt 132447-132428) | Quantification of DNA of SeUS2-A |
| Sfie0.1 (Forward) | 5'-ATGAGTATTAAT CATGATTC-3' (SEQ ID NO: 3) | ie0 gene of SfNIC-B (nt 130128-130147) | Quantification of DNA of SfNIC-C. |
| Sfie0.2 (Reverse) | 5'-TCTTGGCAAATG TTACACTG-3' (SEQ ID NO: 4) | ie0 gene of SfNIC-B (nt 129612-129631) | Quantification of DNA of SfNIC-C. |
| qSe5.F (Forward) | 5'-AGCAGCGAGCCA ATGCAGTA-3' (SEQ ID NO: 5) | sf5 gene of SeUS2-A (nt 6274-6293) | Quantification of DNA of SeUS2-A (qPCR). |
| qSe5.R (Reverse) | 5'-CTTCTTGCAACC GCTCGTTC-3' (SEQ ID NO: 6) | se5 gene of SeUS2-A (nt 6354-6373) | Quantification of DNA of SeUS2-A (qPCR) |
| qSfCcath.2F (Forward) | 5'-ACGCCGCGTTTA GTAACAGC-3' (SEQ ID NO: 7) | proximity of the deleted region of SfNIC-C (nt 18717-18736) | Quantification of DNA of SfNIC-C (qPCR). |
| qSfCsf36.2R (Reverse) | 5'-TAAAACTATTTC TTGCAATC-3' (SEQ ID NO: 8) | proximity of the deleted region of SfNIC-C (nt 35150-35169) | Quantification of DNA of SfNIC-C (qPCR),. |
| Ac.1 (Forward) | 5'-GATTTGTTGGCC GAATAACG-3' (SEQ ID NO: 9) | unique gene ac97 of AcC6 (nt 84850-84869) | Quantification of DNA of AcC6 (qPCR). |
| Ac.2 (Reverse) | 5'-TGACTCTTTCAC CCATTGCAG-3' (SEQ ID NO: 10) | unique gene ac97 of AcC6 (nt 84958-84938) | Quantification of DNA of AcC6 (qPCR). |
| Sf.1 (Forward) | 5'-ACGCCGTTCAAA GACACGAG-3' (SEQ ID NO: 11) | unique gene sf43 of SfNIC-B (nt 42832-42851) | Quantification of DNA of SfNIC-B (qPCR). |

TABLE 1-continued

| Primers | Sequences | Localization of fragment to amplfiy (nucleotides in the genome) | Amplification purpose |
|---|---|---|---|
| Sf.2 (Reverse) | 5'-CCGCTTTGCCTT CGACATAG-3' (SEQ ID NO: 12) | unique gene sf43 of SfNIC-B (nt 42976-42957) | Quantification of DNA of SfNIC-B (qPCR) |
| AcDNApol.1 (Forward) | 5'-CAAATGTAGAAT CTGTGTCG-3' (SEQ ID NO: 13) | DNA polymerase gene of AcC6 (nt 53264-53283) | Detection of AcC6 DNA in cell culture plaques,. |
| AcDNApol.2 (Reverse) | 5'-CAGCCATCACAA ACACGCGC-3' (SEQ ID NO: 14) | DNA polymerase gene of AcC6 (nt 53968-53949) | Detection of AcC6 DNA in cell culture plaques |
| SfDNApol.3 (Forward) | 5'-CAACGACATCA TAGAGTGC-3' (SEQ ID NO: 15) | DNA polymerase gene of SfNIC-B (nt 88358-88377) | Detection of SfNIC-B DNA in cell culture plaques |
| SfDNApol.4 (Reverse) | 5'-AAATATTGCTAA GCACATCG-3' (SEQ ID NO: 16) | DNA polymerase gene of SfNIC-B (nt 89322-89303) | Detection of SfNIC-B DNA in cell culture plaques |

DNA Extraction, Digestion and Analysis

Virions were released from OBs by mixing 100 µl of OB suspension containing $10^9$ OBs/ml with 100 µl 0.5 M $Na_2CO_3$, 50 µl 10% (w/v) sodium dodecyl sulfate in a final volume of 500 µl and incubating for 10 min at 60° C. Undissolved OBs and other debris were removed by low-speed centrifugation (3,800×g, 5 min). The supernantant containing the virions was treated with 25 µl proteinase K (20 mg/ml) for 1 hour at 50° C. Viral DNA was extracted twice with saturated phenol and once with chloroform and isolated from the aqueous phase by alcohol precipitation. The pellet was suspended in 50 to 100 µl of 0.1×TE buffer (Tris-EDTA, pH 8) for 10 min at 60° C. DNA concentration was estimated by reading the optical absorption at 260 nm.

For restriction endonuclease analysis, 2 µg of viral DNA were mixed with 10 U of the enzyme PstI (Takara) and incubated for 12 h at 37° C. Reactions were stopped by addition of 4 µl of loading buffer (0.25% w/v bromophenol blue, 40% w/v sucrose). Electrophoresis was performed using horizontal 1% agarose gels in TAE buffer (0.04 M Tris-acetate, 0.001 M EDTA, pH 8.0) at 20 V for 10 to 24 h. DNA fragments were stained with ethidium bromide and visualized on a UV transilluminator (Chemi-Doc, BioRad, California, USA).

Example 1: Compatibility Between Pif Genes of *S. exigua* MNPV (SeMNPV) and *S. frugiperda* MNPV (SfMNPV)

In this example we present evidence that two species of baculoviruses can replicate in the same cell and can share two proteins (PIF1 and PIF2) that are located in the ODV and are essential for peroral transmission of baculoviruses.

A) the Two Viruses Used in the Assays of the Present Example are as Follows:

*Spodoptera exigua* MNPV (SeMNPV), SeUS2-A variant. The SeUS2-A variant of SeMNPV originates from the SeUS-2 isolate from Florida that is the basis for the insecticide Spod-X® (Certis USA, LLC) bioinsecticide which comprises a heterogeneous mixture of at least four genotypic variants (Muñoz et al., 1999) of the nucleopolyhedrovirus SeMNPV, that infects and kills larvae of the beet armyworm, *Spodoptera exigua*. The SeUS2-A was obtained by in vivo cloning in larvae of *S. exigua* that ingested a low dose ($LD_{10}$) of OBs that killed approximately 10% of treated larvae. SeUS2-A is the most abundant variant present in the SeUS2 isolate and is only infective for *S. exigua* larvae. This variant can also replicate in vitro in the Se301 cell line.

*Spodoptera frugiperda* MNPV (SfMNPV), SfNIC-C variant. The SfNIC-C variant originates from a Nicaraguan isolate of SfMNPV that comprises a heterogeneous mixture of at least nine genotypic variants (Simón et al., 2004b), that have been genetically and phenotypically characterized (Simón et al., 2005a,b; 2011; 2012). SfNIC-C was isolated by in vitro cloning in Sf9 cells (Simón et al., 2004b). This variant has a ~16 kb genomic deletion that eliminates the pif1 and pif2 genes, that means that this variant is not infective by ingestion, although it can produce a productive infection following injection of the inoculum into susceptible host insects. This variant can also replicate in the cell lines Sf21 and Sf9.

Both SeMNPV and SfMNPV belong to a phylogenetically related group of alphabaculoviruses (Group II; Herniou et al., 2004), but differ in the host species that they can infect. SeMNPV is specific to *S. exigua* larvae, whereas SfMNPV normally infects *S. frugiperda* larvae but can infect *S. exigua* larvae. Lethal infection of *S. exigua* by SfMNPV results in the production of few OBs and the insect tegument does not disintegrate following death (Simón et al., 2004a).

B) Differentiation of SeUS2-A and SfNIC-C by Restriction Endonuclease Analysis of Genomic DNA.

SeUS2-A and SfNIC-C can be differentiated by treatment of genomic DNA with the restriction endonuclease PstI (Takara), followed by electrophoresis in an agarose gel. The restriction profiles obtained from each genomic DNA are clearly distinct and allow the identification of the presence of one (or both) of said genomes in a sample (see FIG. 2).

C) Pif1/Pif2 Complementation Assays Using SeUS2-A and the Deletion Genotype SfNIC-C.

Fourth instars of *S. exigua* were inoculated by intra-haemocoelic injection of a mixture of SeUS2-A and SfNIC-C ODVs (obtained by mixing equal numbers of OBs of each virus). Injected larvae were individually reared on semi-synthetic diet based on wheat germ, yeast and soybean as described by Greene et al. (1976) until death and the resulting OBs were collected by the method previously described (Caballero et al., 1992). In brief, they were extracted from dead larvae after the homogeneization of the cadavers in sterile water and purification from the resulting suspension by filtration and differential centrifugation.

Analysis of the DNA extracted from these OBs was consistent with the presence of the SeUS2-A variant, but no evidence of SfNIC-C was observed in the restriction profile (FIG. 3, lanes 3 and 5 corresponding to the first and second repetition of the same assay). However, PCR amplification using variant-specific primers (Table 1: Sfie0.1 and Sfie0.2, that is, SEQ ID NO:3 and SEQ ID NO:4) revealed that small quantities of SfNIC-C genomic DNA were present in DNA extracted from the OBs produced in injected S. exigua larvae (FIG. 4, lanes 3 and 5).

These OBs were fed to S. frugiperda second instars at concentrations of $10^7$ and $10^9$ OBs/mL. When inoculated larvae were reared individually on diet, mortalities due to polyhedrosis disease of 30% and 50% were observed, respectively. PCR and PstI analyses of the DNA from the OBs collected from virus-killed S. frugiperda larvae were consistent with the presence of SfNIC-C genotype alone; no evidence was observed to indicate the presence of SeUS2-A DNA. This result was confirmed using the highly sensitive quantitative (real time) PCR technique (qPCR) with genotype-specific primers (Seie0.1 and Seie0.2, respectively, SEQ ID NO.1 and SEQ ID NO:2): no amplification of genome fragments of SeUS2-A was detected (see FIG. 4, lanes 10 and 12).

These results demonstrate that SeUS2-A was not able to replicate in S. frugiperda larvae, which resulted in the elimination of the SeUS2-A variant from the experimental mixed virus population. These results also demonstrate that the SfNIC-C genotype was capable of taking advantage of PIF1 and PIF2 proteins produced by SeUS2-A to initiate primary infection in the midgut cells of perorally inoculated S. frugiperda larvae, which would not be possible in the absence of these proteins. Therefore, the only way in which ODVs containing SfNIC-C could have acquired the PIF1 and PIF2 proteins would be if both SfNIC-C and SeUS2-A replicated simultaneously in the same S. exigua cell. An alternative hypothesis involving recombination of the pif-1/pif-2 region between the genomes of each of these virus was rejected because the second generation of OBs produced in S. frugiperda larvae (comprising the SfNIC-C genotype alone) was not infective per os in S. frugiperda larvae, indicating that PIF1 and PIF2 proteins had not been produced by the SfNIC-C genotype following the inoculation of the OBs produced in coinfected S. exigua larvae.

Thus, in this way, the present inventors have demonstrated co-infection of S. exigua cells by two closely related species of baculoviruses: SeMNPV and SfMNPV.

From these results it can be concluded that:
(a) A cell of S. exigua can be simultaneously infected by two virus species, both of which can replicate.
(b) The PIF1 and PIF2 proteins can rescue the per os infectivity of SfNIC-C (that lacks these pif genes) in S. frugiperda larvae.

D) Persistence of SeUS2-A and SfNIC-C Occluded in Mixed Virus OBs Following Successive Passage in Spodoptera exigua Larvae Mixed virus OBs produced in larvae that had been injected with mixtures of ODVs of SeUS2-A and SfNIC-C (see Section C) were used as inoculum (Passage 0, $P_0$: obtained by co-infection of S. exigua larvae using ODVs released from 1:1 ratio mixtures of SeUS2-A OBs and SfNIC-C OBs) in an experiment involving six successive passages ($P_1$ to $P_6$) in S. exigua larvae per os.

To determine changes in the relative abundance of each of these viruses in OBs collected at each passage ($P_0$-$P_6$) DNA was extracted from OB samples and subjected to qPCR with SYBR Green (Takara) in an ABI PRISM 7900HT thermocycler. DNA was extracted from OBs sampled at each passage and subjected to qPCR quantification; results shown as nanograms of SfNIC-C genomic DNA per 100 nanograms of SeUS2-A genomic DNA.

For amplification of SeUS2-A DNA specific primers were used (qSe5.F and qSe5.R, SEQ ID NO:5 and SEQ ID NO:6, respectively) targeted at the se5 gene that is unique to SeMNPV. Amplification of SfNIC-C DNA was achieved using specific primers (qSfCcath.2F and qSfCsf36.2R, SEQ ID NO: 7 and SEQ ID NO:8, respectively) that amplified 50 nucleotides (nt) upstream and downstream of the 16 kb deletion in this virus. Calibration curves were generated by amplification of plasmid DNA containing cloned fragments of SeUS2-A or SfNIC-C DNA, using the previously mentioned pairs of primers. Plasmid DNA was quantified by spectrophotometry and subjected to ten-fold serial dilution to produce a calibration curve in the region $10^{-1}$ ng a $10^{-9}$ ng DNA. The primer hybridization temperature was 60° C. and elongation time was 30 seconds.

Figure 5:
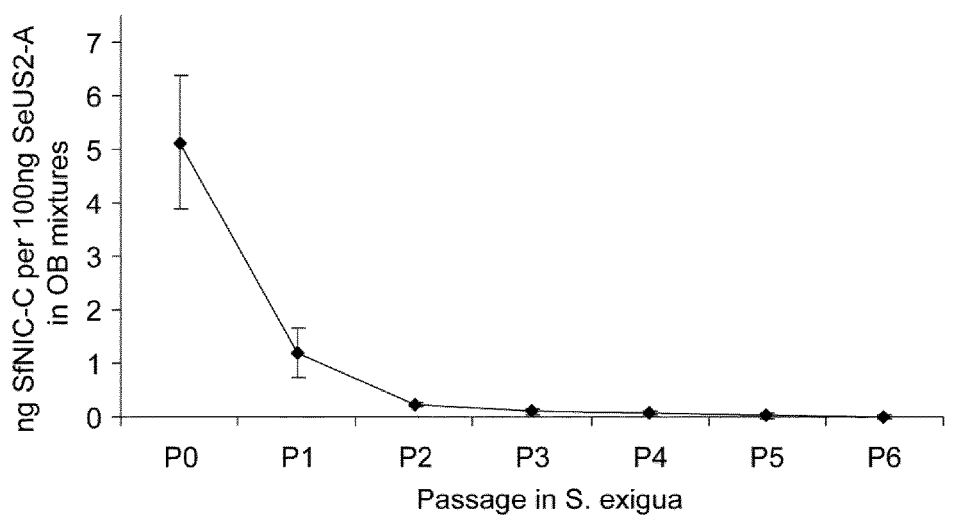

DNA extracted from single virus OBs only produced positive amplification in qPCR reactions involving the primers that targeted the corresponding virus. DNA samples extracted from OBs of $P_0$ were estimated to comprise 95.13±1.25% (mean±standard error [SE]) of SeUS2-A DNA and 4.87±1.25% of SfNIC-C DNA. The percentage of SfNIC-C DNA extracted from OBs sampled at $P_1$, $P_2$, $P_3$, $P_4$, $P_5$ and $P_6$ declined progressively with values of 1.17±0.45%, 0.23±0.04%, 0.10±0.06, 0.09±0.04%, 0.03±0.01% and 0.01±0.004%, respectively (FIG. 5).

Example 2: Co-Occlusion and Co-Wrapping of the Genomes of Two Baculovirus Species The two viruses used in these experiments were as follows:

Autographa californica multiple nucleopolyhedrovirus (AcMNPV). AcMNPV is the type species of the genus Alphabaculovirus. It is a multicapsid virus that belongs to Group I NPVs, that are characterized by the presence of a glycoprotein (GP64) in the BV membrane. In the present study the cloned genotype AcC6 was used, which was the first baculovirus genome that was completely sequenced (GenBank accession number L22858; Ayres et al., 1994). This virus replicates well in Sf21 and Sf9 cell lines and can produce a productive lethal infection in S. frugiperda larvae.

Spodoptera frugiperda multiple nucleopolyhedrovirus (SfMNPV). This is a Group II NPV that is characterized by the presence of F protein in the BV (Herniou et al., 2004), and is therefore phylogenetically distant from AcMNPV. In the present study an in vitro clone was used, named SfNIC-B, that was the most abundant genotype present in the wild-type isolate from Nicaragua (SfNIC) (Simón et al., 2004b). SfNIC-B is a complete genome (GenBank accession number HM595733.1, Simón et al., 2012) and is infective per os to S. frugiperda larvae A) Production of Mixed Virus ODVs and OBs that Contain the Genomes of SfNIC-B and AcMNPV To produce mixed virus ODVs and OBs, S. frugiperda fourth instars were inoculated with mixtures of SfNIC-B OBs and AcMNPV OBs in a 1:1 ratio at a concentration of $5 \times 10^7$ OB/ml of each virus, using the droplet feeding method (Hughes & Wood, 1986). Larvae of S. frugiperda are susceptible to both viruses. Groups of 24 larvae were inoculated and the experiment was performed three times. Inoculated larvae were individually reared on the semi-synthetic laboratory diet also used in Example 1 at controlled temperature (25° C.) in darkness until death. OBs were collected from infected cadavers and purified by filtration and centrifugation as described previously (Muñoz et al., 1998).

To confirm the presence of both viruses in these OBs, genomic DNA was extracted and subjected to PCR amplification using SfDNApol.3 (SEQ ID NO: 15) and SfD-NApol.4 (SEQ ID NO:16) primers to amplify SfNIC-B DNA, or AcDNApol.1 (SEQ ID NO:13) and AcDNApol.2 (SEQ ID NO:14) primers to amplify AcMNPV DNA.

Figure 6:
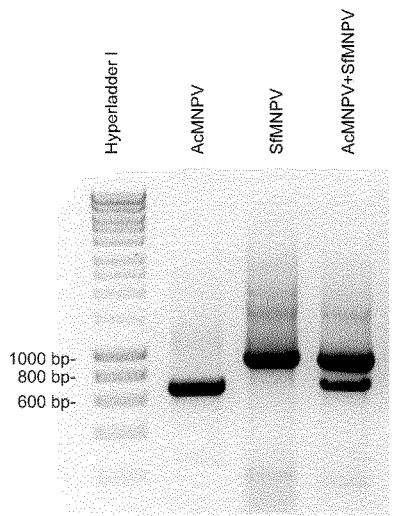

Amplification of AcMNPV DNA resulted in a product of 704 bp, whereas amplification of SfNIC-B DNA resulted in a product of 964 bp (FIG. 6). Detection of the presence of genomic DNA of both viruses in DNA samples extracted from OBs demonstrates that both viruses replicated in the inoculated insects.

To demonstrate co-wrapping of both viruses in ODVs and co-occlusion in OBs, ODVs were released by treatment of OB suspension ($10^8$ OB/ml) by alkaline lysis using an equal volume of 0.1 M sodium carbonate solution during 30 minutes at 28° C. ODVs were subjected to plaque assay using Sf9 cells (Invitrogen, Cat no. B825-01) as previously described (King et al., 1992). For this, serial dilutions ($10^{-1}$-$10^{-6}$) were performed and volumes of 200 µl of each suspension were placed onto $10^6$ Sf9 cells in the wells of a cell culture dish. Inoculated cells were incubated on an orbital shaker for 1 hour. The medium was then removed and 2 ml of 1% agarose in TC100 with 10% foetal calf serum was placed in each well. Cell culture plates were then incubated at 28° C. for 5-6 days. Clearly isolated plaques were picked, treated with proteinase K and analyzed by PCR using SfNIC-B specific primers (SfDNApol.3 and SfD-NApol.4) or AcMNPV specific primers (AcDNApol.1 and AcDNApol.2).

Overall, following three repetitions, 3.82±2.73% (mean±standard deviation) of clones comprised AcMNPV alone, whereas approximately 48.1±8.9% of plaques comprised SfNIC-B alone and the remaining approximately 48.1±6.5% of plaques comprised a mixture of both viruses. The results obtained in each repetition of the assay and the average (±standard deviation) are indicated in Table 2 below.

TABLE 2

| Virus | Repetition 1 % (n) | Repetition 2 % (n) | Repetition 3 % (n) | Average ± S.D. |
|---|---|---|---|---|
| AcMNPV | 8.06 (5) | 0.98 (1) | 4.08 (4) | 3.8 ± 2.7 |
| SfMNPV | 32.2 (20) | 53.9 (55) | 52.0 (51) | 48.1 ± 8.9 |
| Co-occluded | 59.6 (37) | 45.1 (46) | 43.9 (43) | 48.1 ± 6.5 | n is the number of cell culture plaques analyzed with presence of either AcMNPV, SfMNPV or both viruses in each of the repetitions performed. S.D. indicates the standard deviation.

Figure 7:
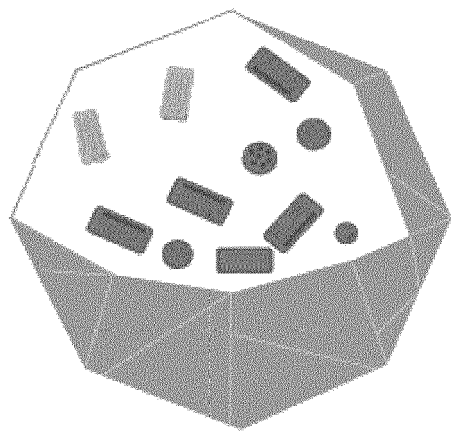

A diagrammatic example of a mixed virus OB occluding the obtained mixed virus ODVs can be seen in FIG. 7. This would only be possible if both viruses were present in the same ODV, which demonstrates that both viruses replicated in the same cell, were co-wrapped in the same ODV and co-occluded in the same OB.

These results were confirmed statistically by end point dilution assay in Sf9 cells (King et al, 1992). Infection by a single ODV was achieved following infection of Sf9 cells with low concentrations of ODVs. Accordingly, the probabilities with which wells were not inoculated with an infective dose of ODV can be calculated according to the Poisson distribution. For this, ODVs were released from a suspension of $10^9$ OB/ml obtained from S. frugiperda larvae that died after inoculation with both viruses. The results of end point dilution assays of these ODVs are presented in Table 3.

TABLE 3

Results of the end point dilution assay.

| | Repetition 1 | Repetition 2 | Repetition 3 |
|---|---|---|---|
| Positive/Total | 12/80 | 11/90 | 4/86 |
| P(0) | 85% | 88% | 95% |
| P(1) | 14% | 11% | 5% |
| P(2) | 1% | 1% | 1% |
| P(3) | 0% | 0% | 0% |

Positive wells are those that contained at least one cell with pathological signs of baculovirus infection (OBs). P(0) is the calculated probability in each repetition of having a well without signs of infection. P(1), P(2) and P(3) were estimated by the Poisson distribution and refer to the probability for the cells in a particular well for being infected by one, two or three ODVs respectively.

A dilution was selected that resulted in approximately 90% of uninfected wells, which reflects a situation in which a single ODV will be responsible for initiating an infection in approximately 10% of infected wells and two or more ODVs will be responsible for infection in less than 1% of wells.

Figure 8:
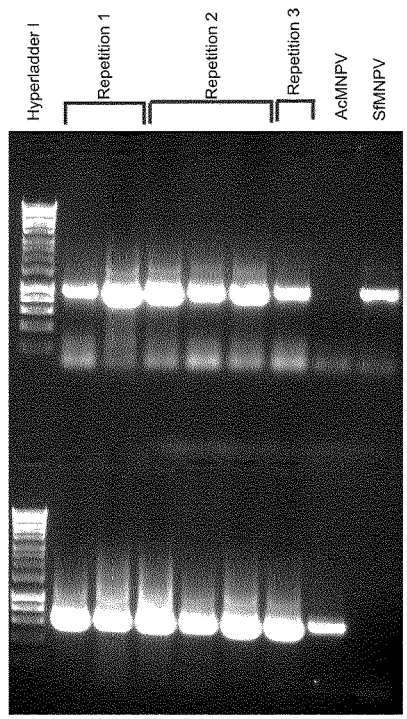

All the wells that were infected at the selected dilution (90% of wells uninfected) were analyzed by PCR as described above. In all cases the presence of both viruses was confirmed (FIG. 8), a situation in which probabilistic theory requires that both viruses were present in the single ODVs that initiated these infections.

Example 3: The Interval Between Inoculation of the First and Second Virus Affects the Prevalence of Co-Wrapping and Co-Occlusion of Different Virus Species in Infected Insects A) The Two Viruses Used in these Experiments were as Follows:
Autographa californica multiple nucleopolyhedrovirus (AcMNPV): cloned genotype AcC6
Spodoptera frugiperda multiple nucleopolyhedrovirus (SfMNPV): cloned genotype SfNIC-B B) Temporal Window of Susceptibility in Dually-Infected S. frugiperda Larvae: Effects on Larval Mortality To determine the effect of interval between infection by two different virus species on insect mortality, recently moulted S. frugiperda fourth instars were orally inoculated with a suspension of $5 \times 10^7$ OB/ml of a first virus using the droplet feeding method (Hughes & Wood, 1986). Inoculated insects were reared individually on semi-synthetic laboratory diet at 25° C. At 12, 24, 48 or 72 h after the first inoculation, these larvae were allowed to feed on the same concentration of OBs of the second virus. In all cases, groups of 24 larvae were used in each treatment and the experiment was performed three times, using AcC6 OBs as the first virus inoculum and SfNIC-B OBs as the second inoculum, and vice versa. Larvae that had been inoculated once or twice were individually reared on semi-synthetic laboratory diet until pupation or death.

Figure 9:
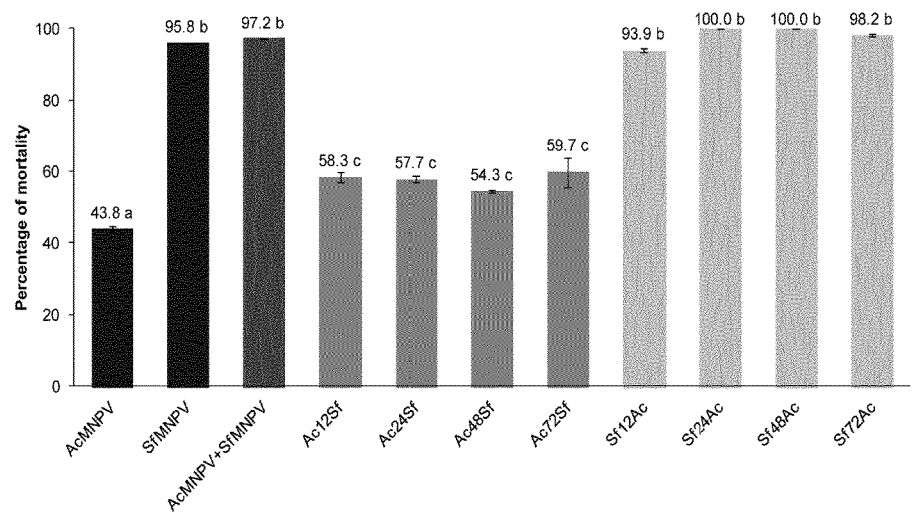
Figure 10:
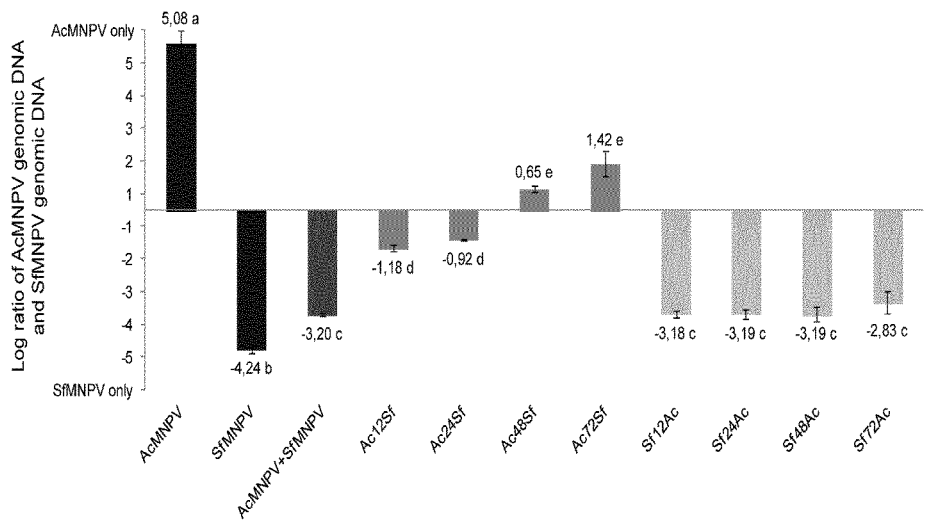
FIG. 10: Log ratio of AcC6 (AcMNPV) genomic DNA and SfNIC-B (SfMNPV) genomic DNA extracted from OBs produced during single infections, simultaneous infection and delayed (12-72 h) superinfections using OB inoculum of each of these viruses. Columns headed by identical letters did not differ significantly (ANOVA, Tukey, p>0.05).
Figure 11:
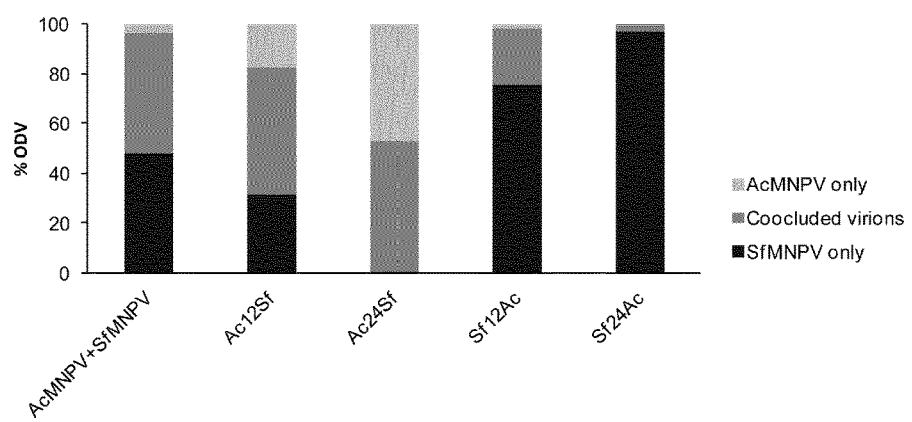
FIG. 11: Composition of ODVs released from mixed virus OBs produced in simultaneous and delayed co-infection experiment.

The prevalence of mortality due to polyhedrosis disease differed significantly between experimental treatments (Analysis of Variance: $F_{10,672}=230$; $p<0.001$) and allowed the treatments to be classified into one of three groups that differed significantly in percentage of mortality (Tukey's honest significance test, $P<0.05$) (FIG. 9):

(i) Larvae treated with AcC6 OBs alone: this treatment resulted in the lowest prevalence of virus mortality.

(ii) Larvae treated with SfNIC-B OBs alone, with simultaneous administration of OBs of both viruses in mixtures, or with SfNIC-B OBs followed by AcMNPV OBs: all of these treatments resulted in a similarly high prevalence of mortality.

(iii) Larvae treated first with AcC6 OBs and subsequently with SfMNPV OBs: the prevalence of mortality was slightly but significantly higher than observed in larvae treated with AcC6 OBs alone.

These results demonstrate that compared to simultaneous infection of both viruses at the same moment, delays of 12-72 h resulted in a marked decrease in the lethal effect of SfNIC-B OBs in insects that had been treated previously with AcC6 OBs. The delay of time between infections is an important factor to optimize the mortality obtained in the production of mixed OBs.

C) Composition of OBs Produced in Larvae Inoculated by Different Species of Virus at Different Intervals.

The temporal interval between the first and second inoculation treatments affected the proportions of each virus in the progeny OBs, as determined by extraction of DNA followed by qPCR quantification of each virus DNA using virus-specific primers (see Table 1) as described previously. Statistical analysis of these results identified the presence of five distinct groups (Analysis of variance: $F_{10,75}$=187.57; p<0.001):

(i) AcC6 alone (ii) SfNIC-B alone (iii) Larvae treated with both viruses simultaneously and all treatments involving initial treatments with SfNIC-B OBs (iv) Larvae treated initially with AcC6 OBs and with SfNIC-B OBs at 12 or 24 h later (v) Larvae treated initially with AcC6 OBs and with SfNIC-B OBs at 48 or 72 h later Larvae initially infected with AcC6 OBs and 24 or 48 hours later with SfNIC-B OBs produced progeny OBs comprising approximately a 1:1 ratio of each virus. When larvae were inoculated with two different virus species, both viruses were invariably present in the progeny OBs collected from virus-killed insects.

D) Effects of Co-Wrapping of Different Virus in ODVs and Co-Inclusion in OBs

The virus composition of ODVs was analyzed by plaque assay as described in Example 2. As the time between the first and second inoculation increased the proportion of genomes (virions) of a single species or of both species together varied according to the interval between inoculations and the identity of the first or second virus (FIG. 11). For example, an inoculation with AcC6 OBs followed 24 h later by inoculation with SfNIC-B resulted in progeny OBs comprising approximately 50% AcC6 genomes and 50% SfNIC-B genomes, with approximately 50% of ODVs comprising both viruses within mixed virus virions.

REFERENCES

Ahn, M., Song, M., Oh, E., Jamal, A., Kim, H., Ko, K., Choo, Y., Kim, B. & Ko, K. (2008) Production of therapeutic proteins with baculovirus expression system in insect cell. *Entomological Research* 38: S71-S78.

Arella, M., Devauchelle, G. & Belloncik, S. (1983) Dual infection of a lepidopterean cell line with the cytoplasmic polyhedrosis virus (CPV) and the Chilo iridescent virus (CIV). *Annales de l'Institut Pasteur/Virologie* 134: 455-463.

Argaud, O., Croizier, L., López-Ferber, M. & Croizier, G. (1998) Two key mutations in the host-range specificity domain of the p143 gene of *Autographa californica* nucleopolyhedrovirus are required to kill *Bombyx mori* larvae. *Journal of General Virology* 79: 931-935.

Ayres, M. D., Howard, S. C., Kuzio, J., López-Ferber, M. & Possee, R. D. (1994) The complete DNA sequence of *Autographa californica* nuclear polyhedrosis virus. *Virology* 202: 586-605.

Burges, H. D., Croizier, G. & Huber, J. (1980) A review of safety tests on baculoviruses. *Entomophaga* 25: 329-339.

Caballero, P., Zuidema, D., Santiago-Alvarez, C., Vlak, J. M., 1992. Biochemical and biological characterization of four isolates of *Spodoptera exigua* nuclear polyhedrosis virus. Biocontrol Science and Technology, 2: 145-157.

Clavijo, G., Williams, T., Simón, O., Muñoz, D., Cerutti, M., López-Ferber, M. & Caballero, P. (2009) Mixtures of complete and pif1- and pif2-deficient genotypes are required for increased potency of an insect nucleopolyhedrovirus. *Journal of Virology* 83: 5127-5136.

Croizier, G., Croizier, L., Argaud, O. & Poudevigne, D. (1994) Extension of *Autographa californica* nuclear polyhedrosis-virus host range by interspecific replacement of a short DNA-sequence in the P143 helicase gene. *Proceedings of the National Academy of Sciences of the United States of America.* 91: 48-52.

Garzon, S. & Kurstak, E. (1972). Infection double inhabituelle de cellules d'un arthropode par le virus de la polyédrie nucléaire (VPN) et le virus irisant de Tipula (TIV). *Comptes Rendus de l'Academie des Sciences. D* 275, 507-509.

Gröner. A. 1986. Specificity and safety of baculoviruses. In *The Biology of Baculoviruses*. Vol. I. Granados, R. R. and Federici, B. A. (eds). Boca Raton, Fla.: CRC Press, pp. 177-202.

Hamblin, M., Vanbeek, N. A. M., Hughes, P. R. & Wood, H. A. (1990) Coocclusion and persistence of a baculovirus mutant lacking the polyhedrin gene. *Applied and Environmental Microbiology* 56: 3057-3062.

Harper, D. M. 2009. Currently approved prophylactic HPV vaccines. Expert Review of Vaccines 8: 1663-1679.

Herniou, E. A., Olszewski, J. A., O'Reilly, D. R. & Cory, J. S. (2004) Ancient coevolution of baculoviruses and their insect hosts. *Journal of Virology* 78: 3244-3251.

Hitchman, R. B., Locanto, E., Possee, R. D. & King, L. A. (2011) Optimizing the baculovirus expression vector system. *Methods* 55: 52-57.

Hughes, P. R. & Wood, H. A. (1986) In vivo and in vitro bioassay methods for baculoviruses. In *The Biology of Baculoviruses*. Vol. II. Granados, R. R. and Federici, B. A. (eds). Boca Raton, Fla.: CRC Press, pp. 1-30.

Inceoglu, A. B., Kamita, S. G., & Hammock, B. D. (2006) Genetically modified baculoviruses: a historical overview and future outlook. *Advances in Virus Research.* 68: 323-360.

Jarvis, D. L. Baculovirus-insect cell expression systems (2009). *Methods Enzymol.* 463:191-222.

Jiang, H., Han, Y., Hu, L., Zhang, J. & Hu, Y. (2008) Advances in application of recombinant insect viruses as biopesticides. *Acta Entomologica Sinica* 51: 322-327.

Kaikkonen, M. U., Yla-Herttuala, S. & Airenne, K. J. (2011) How to avoid complement attack in baculovirus-mediated gene delivery. *Journal of Invertebrate Pathology* 107: S71-S79.

Kamita, S. G. & Maeda, S. (1996) Abortive infection of the baculovirus *Autographa californica* nuclear polyhedrosis virus in Sf-9 cells after mutation of the putative DNA helicase gene. *Journal of Virology* 70: 6244-6250.

Kanthong, N., Khemnu, N., Pattanakitsakul, S.-N., Malasit, P. & Flegel, T. (2010) Persistent, triple-virus co-infections in mosquito cells. *BMC Microbiology* 10: 14.

Kantoff, P. W., Higano, C. S., Shore, N. D. Berger, E. R. Small, E. J. Penson, D. F., Redfern, C. H., Ferrari, A. C., Dreicer, R. Sims, R. B. et al. 2010. Sipuleucel-T immunotherapy for castration-resistant prostate cancer. *New England Journal of Medicine* 363: 411-422.

King, L. A. & Possee, R. (1992) The baculovirus expression system. A laboratory guide. London, United Kingdom: Chapman & Hall.

Kondo, A. & Maeda, S. (1991) Host range expansion by recombination of the baculoviruses *Bombyx mori* nuclear polyhedrosis-virus and *Autographa californica* nuclear polyhedrosis-virus. *Journal of Virology* 65: 3625-3632.

Leuschner, R. G. K., Robinson, T. P., Hugas, M., Coccocelli, P. S., Richard-Forget, F., Klein, G., Licht, T. R., Nguyen—The, C., Querol, A., Richardson, M., Suarez, J. E., Thrane, U., Vlak, J. M. & von Wright, A. (2010) Qualified presumption of safety (QPS): a generic risk assessment approach for biological agents notified to the European Food Safety Authority (EFSA). *Trends in Food Science & Technology* 21: 425-435.

Lynn D. E. (2007) Available lepidopteran insect cell lines. Methods in molecular biology (Clifton, N.J.) 388: 117-138.

López-Ferber, M., Simón, O., Williams, T., Caballero, P. (2003). Defective or effective? Mutualistic interactions between virus genotypes. *Proceedings of the Royal Society B* 270: 2249-2255.

Madhan, S., Prabakaran, M. & Kwang, J. (2010) Baculovirus as vaccine vectors. *Current Gene Therapy* 10: 201-213.

McClintock, J. T. & Dougherty, E. M. (1987) Superinfection of baculovirus-infected gypsy-moth cells with the nuclear polyhedrosis viruses of *Autographa californica* and *Limantria dispar*. *Virus Research* 7: 351-364.

Miller, D. W. (1991) Mixed baculovirus compositions and uses thereof. U.S. Pat. No. 5,071,748. Isued Dec. 10, 1991.

Moscardi, F. (1999) Assessment of the application of baculoviruses for control of Lepidoptera. *Annual Review of Entomology* 44: 257-289.

Muñoz, D., Castillejo, J. I. & Caballero, P. (1998) Naturally occurring deletion mutants are parasitic genotypes in a wild-type nucleopolyhedrovirus population of *Spodoptera exigua*. *Applied and Environmental Microbiology* 64: 4372-4377.

Parks, W. P., Casazza, A. M., Alcott, J. & Melnick, J. L. (1968) Adeno-associated satellite virus interference with replication of its helper. *Journal of Experimental Medicine* 127: 91-108.

Rohrmann, G. F. (2008) Baculovirus Molecular Biology. Bethesda, Md.: National Library of Medicine, USA.

Salem, T., Cheng, X. H. & Cheng X. W. (2012) AcMNPV enhances infection by ThorNPV in Sf21 cells and SeMNPV in Hi5 cells. *Archives of Virology* 157: 1875-1885.

Simón, O., Williams, T., López-Ferber, M. & Caballero, P. (2004a) Virus entry or the primary infection cycle are not the principal determinants of host specificity of *Spodoptera* spp. nucleopolyhedroviruses. *Journal of General Virology* 85: 2845-2855.

Simón, O., Williams, T., López-Ferber, M. & Caballero, P. (2004b) Genetic structure of a *Spodoptera frugiperda* nucleopolyhedrovirus population: High prevalence of deletion genotypes. *Applied and Environmental Microbiology*. 70: 5579-5588.

Simón, O., Williams, T., López-Ferber, M. & Caballero, P. (2005a) Functional importance of deletion mutant genotypes in an insect nucleopolyhedrovirus population. *Applied and Environmental Microbiology* 71: 4254-4262.

Simón, O., Chevenet, F., Williams, T., Caballero, P. & López-Ferber, M. (2005b) Physical and partial genetic map of *Spodoptera frugiperda* nucleopolyhedrovirus (Sf-MNPV) genome. *Virus Genes* 30: 403-417.

Simón, O., Palma, L., Beperet, I., Muñoz, D., López-Ferber, M., Caballero, P. & Williams, T. (2011) Sequence comparison between three geographically distinct *Spodoptera frugiperda* multiple nucleopolyhedrovirus isolates: Detecting positively selected genes. *Journal of Invertebrate Pathology* 107: 33-42

Simón, O., Palma, L., Williams, T., López-Ferber, M. & Caballero, P. (2012) Analysis of a naturally-occurring deletion mutant of *Spodoptera frugiperda* multiple nucleopolyhedrovirus reveals sf58 as a new per os infectivity factor of lepidopteran-infecting baculoviruses. *Journal of Invertebrate Pathology* 109: 117-126.

Summers, M. D. & Smith, G. E. (1987) A manual of methods for baculovirus vectors and insect cell-culture procedures. *Texas Agricultural Experiment Station Bulletin:* 1-56.

Sun, X. l. & Peng, H. Y. (2007) Recent advances in biological control of pest insects by using viruses in China. *Virologica Sinica* 22: 158-162.

Van Oers, M. 2011. Opportunities and challenges for the baculovirus expression system. *Journal of Invertebrate Pathology* 107: S3-S15.

Watanabe, S., Ohta, M., Kokuho, T., Mori, H. & Inumaru, S. (2010) Rapid and accurate method for isolation of recombinant baculovirus with an expanded host range. *Journal of Bioscience and Bioengineering* 110: 66-68.

Yanase, T., Yasunaga, C., Hara, T. & Kawarabata, T. (1998) Coinfection of *Spodoptera exigua* and *Spodoptera frugiperda* cell lines with the nuclear polyhedrosis viruses of *Autographa californica* and *Spodoptera exigua*. *Intervirology* 41: 244-252.

The invention claimed is:

1. A method for producing virus occlusion bodies (OBs) in which at least one mixed virus occlusion derived virion (ODV) that comprises genomes from at least two different baculovirus species is occluded, comprising:
   a) co-infecting larvae or culture cells of an insect species with the baculovirus genomes to be co-wrapped in the at least one produced occlusion derived virion, wherein each baculovirus genome belonging to one particular species can be in the same ODV or in a different ODV than the other one;

b) rearing the infected larvae or cultivating the cells until death by polyhedrosis;

c) isolating the produced OBs from the larvae or cultivated cells after their death;

wherein the cells or larvae are susceptible to infection by the at least two different baculoviruses whose genomes are to be co-wrapped in the at least one produced occlusion derived virion, and wherein at least one of the infecting baculoviruses is a multiple nucleopolyhedrovirus.

2. The method according to claim 1, wherein the infecting baculoviruses are all multiple nucleopolyhedroviruses.

3. The method according to claim 1, wherein at least two of the different genomes comprised in a same ODV are genomes that are each capable of giving rise to an infective baculovirus particle, and said genomes are each capable of producing a complete viral cycle in a cell without the need for co-infection with a second baculovirus comprising a different genome.

4. The method for producing virus occlusion bodies according to claim 1, wherein the baculovirus genomes in the form of nucleocapsids inoculate the insect cells or insect larvae.

5. The method according to claim 4, wherein the baculovirus genomes in the form of nucleocapsids are wrapped in the form of at least one ODV.

6. The method according to claim 5, wherein the baculovirus genomes in the form of nucleocapsids are wrapped in the form of at least one ODV, and wherein the at least one ODV is occluded in a proteinaceous matrix together with other ODVs in the form of at least one occlusion body.

7. The method according to claim 6, wherein the at least one occlusion body comprises at least one ODV, wherein genomes of more than one species are co-wrapped.

8. The method according to claim 4, wherein the baculovirus genomes belonging to a particular species are inoculated to the insect cells or insect larvae simultaneously with other baculovirus genome(s) to form nucleocapsids, and said nucleocapsids are then wrapped to form at least one occlusion-derived virion.

9. The method according to claim 4, wherein the baculovirus genomes in the form of nucleocapsids are inoculated to the insect larvae.

10. The method according to claim 1, wherein two different baculovirus species are inoculated.

11. The method according to claim 1, wherein a proportion of genomes from the at least two different baculovirus species is 1:1.

12. A method for producing mixed OBs comprising the steps of:
    a) co-infecting insect larvae with two different baculovirus species, by simultaneous inoculation, or sequential inoculation with a delay of time inferior to the time necessary for the manifestation of the signs of the first infection, and
    b) rearing the inoculated larvae in the conditions necessary until evident disease or death by polyhedrosis.

13. The method according to claim 12, wherein said baculovirus species comprises a variant SeUS2-A of the *Spodoptera exigua* multiple nucleopolyhedrovirus (SeMNPV) and a variant SfNIC-C of *Spodoptera frugiperda* multiple nucleopolyhedrovirus (SfMNPV), and further wherein both of said baculovirus species co-infect fourth instar *Spodoptera exigua* larvae, and said larvae are subsequently reared until evident disease or death by polyhedrosis.

14. The method according to claim 13, wherein both baculoviruses are inoculated simultaneously to the larvae by haemocoelic injection of a 1:1 mixture of ODVs of each baculovirus.

15. The method according to claim 1, wherein said baculovirus species comprises a variant AcC6 of *Autographa californica* multiple nucleopolyhedrovirus (AcMNPV) and a variant SfNIC-B of *Spodoptera frugiperda* multiple nucleopolyhedrovirus (SfMNPV), and further wherein both of said baculovirus species co-infect *Spodoptera frugiperda* larvae, and said larvae are subsequently reared until death by polyhedrosis.

16. The method according to claim 15, wherein both baculoviruses are inoculated simultaneously to the larvae by oral inoculation of a 1:1 mixture of OBs of each baculovirus.

17. The method according to claim 9, wherein the produced OBs are isolated by grinding the dead larvae in water, filtering the resulting suspension, allowing or causing the OBs to separate from the suspension and settle down by sedimentation, centrifugation or a related technique, and separating the pellet of OBs from the supernatant.

18. The method according to claim 17, wherein the isolated OBs are resuspended in an aqueous solution.

19. The method according to claim 18, wherein the aqueous suspension of OBs is stored at room temperature or under refrigeration (0° to 6° C.) prior to formulation.

20. The method according to claim 18, wherein the aqueous suspension of OBs is lyophilized and stored at room temperature or under refrigeration.

21. A mixed virus occlusion derived virion (ODV) that comprises genomes from at least two different baculovirus species co-wrapped in the same virion.

22. A mixed virus occlusion derived virion (ODV) that comprises genomes from at least two different baculovirus species co-wrapped in the same virion, which has been obtained by the method of claim 1.

23. The ODV according to claim 21, which contains at least a genome copy of the variant AcC6 of AcMNPV and at least a genome copy of the variant SfNIC-B of SfMNPV.

24. A mixed virus OB comprising at least one mixed virus occlusion derived virion of claim 21, wherein said virion is occluded.

25. A mixed virus OB comprising at least one occlusion derived virion (ODV), wherein said virion is occluded, and wherein the ODV is a mixed virus ODV that comprises genomes from at least two different baculovirus species co-wrapped in the same virion, which has been obtained by the method of claim 1.

26. A composition comprising either mixed virus ODV of claim 21, or mixed virus OB comprising occluded ODVs, wherein at least one of the ODVs occluded in mixed virus OBs is a mixed ODV, wherein the mixed ODV comprises two or more nucleocapsids, and wherein the two or more nucleocapsids contain a genome of a different virus species.

27. A composition comprising the mixed virus OB of claim 24.

28. The composition according to claim 27, which additionally comprises mixed virus occlusion derived virions (ODV) that comprise genomes from at least two different baculovirus species co-wrapped in the same virion.

29. The composition according to claim 27, which additionally comprises OBs, each of them containing genomes of a single species.

30. The composition according to claim 29, which is in the form of a suspension or in solid form.

31. The composition according to claim 27, which additionally comprises an agriculturally suitable excipient.

32. The composition according to claim 27, which additionally comprises a fertilizer, or another pesticide.

33. A method for controlling infestation of a substrate by insect pests comprising:
    applying the mixed virus OB of claim 24 to said substrate.

34. The method of claim 33, wherein the substrate is a plant, a crop, a cultivation field or a stored product.

35. A method for controlling infestation of a substrate by insect pests comprising:
    applying the composition of claim 27 to said substrate.

36. The method of claim 35, wherein the substrate is a plant, a crop, a cultivation field or a stored product.

37. A method for producing mixed virus occlusion derived virions (ODV) that comprise genomes from at least two different baculovirus species co-wrapped in the same virion, comprising:
    a) co-infecting larvae or culture cells of an insect species with the baculovirus genomes to be co-wrapped in at least one of the produced occlusion derived virions, wherein each baculovirus genome belonging to one particular species can be in the same ODV or in a different ODV than the other one;
    b) rearing the infected larvae or cultivating the cells until death by polyhedrosis;
    c) isolating the produced OBs from the larvae or cultivated cells after their death;
    d) subjecting the produced isolated OBs to alkaline lysis to obtain free, non occluded ODVs,
    wherein the cells or larvae are susceptible to infection by the at least two different baculoviruses whose genomes are to be co-wrapped in at least one of the produced occlusion derived virions, and
    wherein at least one of the infecting baculoviruses is a multiple nucleopolyhedrovirus.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
```

```
<220> FEATURE:
<223> OTHER INFORMATION: Forward primer Seie0.1, for DNA quantification
      of SeUS2-A Based on ie0 gene of SeUS2-A (nt 131937-131959)

<400> SEQUENCE: 1
ctatagctcg acgctcggtg                                                   20

<210> SEQ ID NO 2
<211> LENGTH: 20
<212> TYPE: DNA
<213> ORGANISM: Artificial Sequence
<220> FEATURE:
<223> OTHER INFORMATION: Reverse primer Seie0.2, for DNA quantification
      of SeUS2-A Based on ie0 gene of SeUS2-A (nt 132447-132428)

<400> SEQUENCE: 2
atcgtcttcg ataccgcgag                                                   20

<210> SEQ ID NO 3
<211> LENGTH: 20
<212> TYPE: DNA
<213> ORGANISM: Artificial Sequence
<220> FEATURE:
<223> OTHER INFORMATION: Forward primer Sfie0.1 for DNA quantification
      of SfNIC-C Based on ie0 gene of SfNIC-B (nt 130128-130147)

<400> SEQUENCE: 3
atgagtatta atcatgattc                                                   20

<210> SEQ ID NO 4
<211> LENGTH: 20
<212> TYPE: DNA
<213> ORGANISM: Artificial Sequence
<220> FEATURE:
<223> OTHER INFORMATION: Reverse primer Sfie0.2, for DNA quantification
      of SfNIC-C Based on ie0 gene of SfNIC-B (nt 129612-129631)

<400> SEQUENCE: 4
tcttggcaaa tgttacactg                                                   20

<210> SEQ ID NO 5
<211> LENGTH: 20
<212> TYPE: DNA
<213> ORGANISM: Artificial Sequence
<220> FEATURE:
<223> OTHER INFORMATION: Forward primer qSe5.F, for DNA quantification
      of SeUS2-A (qPCR) Based on sf5 gene of SeUS2-A (nt 6274-6293)

<400> SEQUENCE: 5
agcagcgagc caatgcagta                                                   20

<210> SEQ ID NO 6
<211> LENGTH: 20
<212> TYPE: DNA
<213> ORGANISM: Artificial Sequence
<220> FEATURE:
<223> OTHER INFORMATION: Reverse primer qSe5.R, for DNA quantification
      of SeUS2-A (qPCR) Based on se5 gene of SeUS2-A (nt 6354-6373)

<400> SEQUENCE: 6
cttcttgcaa ccgctcgttc                                                   20

<210> SEQ ID NO 7
<211> LENGTH: 20
<212> TYPE: DNA
<213> ORGANISM: Artificial Sequence
<220> FEATURE:
```

<223> OTHER INFORMATION: Forward primer qSfCcath.2F, for DNA
      quantification of SfNIC-C (qPCR) Based on the proximity of the
      deleted region of SfNIC-C (nt 18717-18736)

<400> SEQUENCE: 7
acgccgcgtt tagtaacagc                                          20

<210> SEQ ID NO 8
<211> LENGTH: 20
<212> TYPE: DNA
<213> ORGANISM: Artificial Sequence
<220> FEATURE:
<223> OTHER INFORMATION: Reverse primer qSfCsf36.2R for DNA
      quantification of SfNIC-C (qPCR) Based on the proximity of the
      deleted region of SfNIC-C (nt 35150-35169)

<400> SEQUENCE: 8
taaaactatt tcttgcaatc                                          20

<210> SEQ ID NO 9
<211> LENGTH: 20
<212> TYPE: DNA
<213> ORGANISM: Artificial Sequence
<220> FEATURE:
<223> OTHER INFORMATION: Forward primer Ac.1, for DNA quantification of
      AcC6 (qPCR) Based on the unique gene ac97 of AcC6 (nt 84850-84869)

<400> SEQUENCE: 9
gatttgttgg ccgaataacg                                          20

<210> SEQ ID NO 10
<211> LENGTH: 21
<212> TYPE: DNA
<213> ORGANISM: Artificial Sequence
<220> FEATURE:
<223> OTHER INFORMATION: Reverse primer Ac.2, for DNA quantification of
      AcC6 (qPCR) Based on the unique gene ac97 of AcC6(nt 84958-84938)

<400> SEQUENCE: 10
tgactctttc acccattgca g                                        21

<210> SEQ ID NO 11
<211> LENGTH: 20
<212> TYPE: DNA
<213> ORGANISM: Artificial Sequence
<220> FEATURE:
<223> OTHER INFORMATION: Forward primer Sf.1 for DNA quantification of
      SfNIC-B (qPCR) Based on the unique gene sf43 of SfNIC-B (nt 42832-
      42851)

<400> SEQUENCE: 11
acgccgttca aagacacgag                                          20

<210> SEQ ID NO 12
<211> LENGTH: 20
<212> TYPE: DNA
<213> ORGANISM: Artificial Sequence
<220> FEATURE:
<223> OTHER INFORMATION: Reverse primer Sf.2 for DNA quantification of
      SfNIC-B (qPCR) Based on the unique gene sf43 of SfNIC-B (nt 42976-
      42957)

<400> SEQUENCE: 12
ccgctttgcc ttcgacatag                                          20

<210> SEQ ID NO 13
<211> LENGTH: 20

```
<212> TYPE: DNA
<213> ORGANISM: Artificial Sequence
<220> FEATURE:
<223> OTHER INFORMATION: Based on DNA polymerase gene of AcC6 (nt 53264-
      53283) Forward primer AcDNApol.1 for detection of AcC6 DNA in cell
      culture plaques

<400> SEQUENCE: 13
caaatgtaga atctgtgtcg                                                    20

<210> SEQ ID NO 14
<211> LENGTH: 20
<212> TYPE: DNA
<213> ORGANISM: Artificial Sequence
<220> FEATURE:
<223> OTHER INFORMATION: Based on DNA polymerase gene of AcC6 (nt 53968-
      53949) Reverse primer AcDNApol.2 for detection of AcC6 DNA in cell
      culture plaques

<400> SEQUENCE: 14
cagccatcac aaacacgcgc                                                    20

<210> SEQ ID NO 15
<211> LENGTH: 20
<212> TYPE: DNA
<213> ORGANISM: Artificial Sequence
<220> FEATURE:
<223> OTHER INFORMATION: Based on DNA polymerase gene of SfNIC-B (nt
      88358-88377) Forward primer SfDNApol.3 for detection of SfNIC-B
      DNA in cell culture plaques

<400> SEQUENCE: 15
caacgacatc aatagagtgc                                                    20

<210> SEQ ID NO 16
<211> LENGTH: 20
<212> TYPE: DNA
<213> ORGANISM: Artificial Sequence
<220> FEATURE:
<223> OTHER INFORMATION: Based on DNA polymerase gene of SfNIC-B (nt
      89322-89303) Reverse primer SfDNApol.4 for detection of SfNIC-B
      DNA in cell culture plaques

<400> SEQUENCE: 16
aaatattgct aagcacatcg                                                    20
```